(12) United States Patent
Talaat et al.

(10) Patent No.: US 11,860,168 B2
(45) Date of Patent: Jan. 2, 2024

(54) BIOMARKERS FOR EARLY DIAGNOSIS AND DIFFERENTIATION OF MYCOBACTERIAL INFECTION

(71) Applicant: Wisconsin Alumni Research Foundation, Madison, WI (US)

(72) Inventors: Adel Mohamed Talaat, Madison, WI (US); Chia-wei Wu, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/555,819

(22) Filed: Aug. 29, 2019

(65) Prior Publication Data

US 2020/0081016 A1  Mar. 12, 2020

Related U.S. Application Data

(60) Provisional application No. 62/728,387, filed on Sep. 7, 2018.

(51) Int. Cl.
*C12Q 1/6851* (2018.01)
*G01N 33/68* (2006.01)
*G01N 33/569* (2006.01)

(52) U.S. Cl.
CPC ....... *G01N 33/6854* (2013.01); *C12Q 1/6851* (2013.01); *G01N 33/5695* (2013.01); *G01N 33/68* (2013.01); *G01N 2800/26* (2013.01); *G01N 2800/50* (2013.01)

(58) Field of Classification Search
None
See application file for complete search history.

(56) References Cited

U.S. PATENT DOCUMENTS

| | | |
|---|---|---|
| 9,446,110 B2 | 9/2016 | Talaat |
| 9,663,758 B2 | 5/2017 | Talaat |
| 10,054,586 B2 | 8/2018 | Talaat |
| 2007/0042383 A1 | 2/2007 | Kapur |
| 2014/0271719 A1 | 9/2014 | Talaat |

FOREIGN PATENT DOCUMENTS

| | | |
|---|---|---|
| WO | 2010132054 | 11/2010 |
| WO | 2014164055 A1 | 10/2014 |
| WO | 2016069612 A2 | 5/2016 |

OTHER PUBLICATIONS

Enard et al. (Science 2002 vol. 296 p. 340) (Year: 2002).*
Cobb et al (Crit Care Med 2002 vol. 30 p. 2711) (Year: 2002).*
International Search Report for PCT/US2019/048893, dated Feb. 3, 2020.
Beisiegel et al. Combination of host susceptibility and *Mycobacterium tuberculosis* virulence define gene expression profile in the host. Eur. J. Immunol. 2009. 39: 3369-3384.
*Mycobacterium paratuberculosis* protein, Seq. ID 5577. GENESEQ, 2008. XP002752570.
Tiwari, A., et al (2006). Johne's disease in Canada Part I: clinical symptoms, pathophysiology, diagnosis, and prevalence in dairy herds. Can Vet J 47(9), 874-882.
Velez, D., et al. (2009). NOS2A, TLR4, and IFNGR1 interactions influence pulmonary tuberculosis susceptibility in African-Americans. Human Genetics 126(5), 643-653.
Verschoor, C.P., et al. (2010). Gene expression profiling of PBMCs from Holstein and Jersey cows sub-clinically Infected with *Mycobacteriumavium*ssp. *paratuberculosis*. Veterinary immunology and immunopathology 137(1-2), 1-11.
Waddell, L.A., et al. (2016). The potential public health impact of *Mycobacterium avium* ssp. *paratuberculosis*: global opinion survey of topic specialists. Zoonoses Public Health 63(3), 212-222. doi: 10.1111/zph.12221.
Walzl, G., et al. (2011). Immunological biomarkers of tuberculosis. Nat Rev Immunol 11(5), 343-354. doi: 10.1038/nri2960.
Waters, W.R., et al. (2015). Interleukin-17A as a biomarker for bovine tuberculosis. Clin Vaccine Immunol 23(2), 168-180. doi: 10.1128/CVI.00637-15.
Whittington, R.J., et al. (2001). Progress towards understanding the spread, detection and control of *Mycobacterium avium*subsp. *paratuberculosis* in animal populations. Australian veterinary journal 79(4), 267-278.
Wu, C.W., et al. (2007). Defining the stressome of *Mycobacterium avium* subsp. *paratuberculosis* in vitro and in naturally infected cows. Journal of Bacteriology 189(21), 7877-7886.
Xi, X., et al. & other authors (2011). A novel strategy to screen Bacillus Calmette-Guerin protein antigen recognized by gammadelta TCR. PLoS One 6, e18809.
Al-Khodari, N. Y., et al (2011). Identification, Diagnostic Potential, and Natural Expression of Immunodominant Seroreactive Peptides Encoded by Five *Mycobacterium tuberculosis*-Specific Genomic Regions. Clinical and Vaccine Immunology 18, 477-482.
Arsenault, R.J., et al. (2012). *Mycobacterium avium* subsp. *paratuberculosis* inhibits gamma interferon-induced signaling in bovine monocytes: insights into the cellular mechanisms of Johne's disease. Infect Immun 80(9), 3039-3048. doi: 10.1128/IAI.00406-12.
Bezos, J., et al. (2010). Experimental infection with *Mycobacterium caprae* in goats and evaluation of immunological status in tuberculosis and paratuberculosis co-infected animals. Veterinary Immunology and Immunopathology 133, 269-275.
Bickhart, D.M., et al. (2017). Single-molecule sequencing and chromatin conformation capture enable de novo reference assembly of the domestic goat genome. Nat Genet 49(4), 643-650. doi: 10.1038/ng.3802.
Blanco, F.C., et al. (2011). Increased IL-17 expression is associated with pathology in a bovine model of tuberculosis. Tuberculosis (Edinb) 91 (1), 57-63. doi: 10.1016/j.tube.2010.11.007.
Cho, J., et al. (2012). Economic analysis of *Mycobacterium avium* subspecies *paratuberculosis* vaccines in dairy herds. Journal of Dairy Science 95(4), 1855-1872. doi: http://dx.doi.org/10.3168/jds.2011-4787.

(Continued)

*Primary Examiner* — Katherine D Salmon
(74) *Attorney, Agent, or Firm* — Quarles & Brady LLP

(57) ABSTRACT

Mycobacterial-specific biomarkers and methods of using such biomarkers for diagnosis of mycobacterial infection in a mammal are disclosed.

10 Claims, 10 Drawing Sheets
(8 of 10 Drawing Sheet(s) Filed in Color)

Specification includes a Sequence Listing.

(56) References Cited

OTHER PUBLICATIONS

Clancy, B.M., et al. (2003). A gene expression profile for endochondral bone formation: oligonucleotide microarrays establish novel connections between known genes and BMP-2-induced bone formation in mouse quadriceps. Bone 33(1), 46-63.

Collins MT, et al. 1994. Herd prevalence and geographic distribution of, and risk factors for, bovine paratuberculosis in Wisconsin. J Am Vet Med Assoc 204:636-641.

Corbaz, A., et al. (2002). IL-18-binding protein expression by endothelial cells and macrophages is up-regulated during active Crohn's disease. J Immunol 168(7), 3608-3616.

Costanzo, M., et al. (2016). A global genetic interaction network maps a wiring diagram of cellular function. Science 353(6306). doi: 10.1126/science.aaf1420.

Coussens, P.M., et al. (2004). Cytokine gene expression in peripheral blood mononuclear cells and tissues of cattle infected with *Mycobacterium avium* subsp. *paratuberculosis*: evidence for an inherent proinflammatory gene expression pattern. Infect Immun 72(3), 1409-1422.

Daniel, R., et al. & Clifton-Hadley, R. (2009). Outbreak of tuberculosis caused by *Mycobacterium bovis* in golden Guernsey goats in Great Britain. Vet rec %19;165, 335-342.

David, J., et al. (2014). Gene expression profiling and putative biomarkers of calves 3 months after infection with *Mycobacterium avium* subspecies *paratuberculosis*. Vet Immunol Immunopathol 160(1-2), 107-117. doi: 10.1016/j.vetimm 2014.04.006.

Dong, Y., et al. (2013). Sequencing and automated whole genome optical mapping of the genome of a domestic goat (*Capra hircus*). Nat Biotechnol 31(2), 135-141. doi: 10.1038/nbt.2478.

Du, X., et al. (2014). An update of the goat genome assembly using dense radiation hybrid maps allows detailed analysis of evolutionary rearrangements in Bovidae. BMC Genomics 15, 625. doi: 10.1186/1471-2164-15-625.

Du, Z., et al. (2010). agriGO: a GO analysis toolkit for the agricultural community. Nucleic Acids Res 38(Web Server Issue), W64-70. doi: 10.1093/nar/gkq310.

Gey Van Pittius, N. C., et al (2012). Infection of African Buffalo (*Syncerus caffer*) by Oryx Bacillus, A Rare Member of the Antelope Clade of the *Mycobacterium tuberculosis* Complex. Journal of Wildlife Diseases 48, 849-857.

Ghosh P, et al. 2014. Virulence and Immunity Orchestrated by the Global Gene Regulator sigL in *Mycobacterium avium* subsp. *paratuberculosis*. Infect Immun 82:3066-3075.

Ghosh P, et al. 2013. Key Role for the Alternative Sigma Factor, SigH, in the Intracellular Life of *Mycobacterium avium* subsp. *paratuberculosis* during Macrophage Stress. Infect. Immun. 81:2242-2257.

Hahn MY, et al. 2005. The *Mycobacterium tuberculosis* extracytoplasmic-function sigma factor SigL regulates polyketide synthases and secreted or membrane proteins and is required for virulence. Journal of Bacteriology. 187:7062-7071.

Halls, M.L., et al. (2010). Sub-picomolar relaxin signalling by a pre-assembled RXFP1, AKAP79, AC2, beta-arrestin 2, PDE4D3 complex. EMBO J 29(16), 2772-2787. doi: 10.1038/emboj.2010.168.

Hein, M.Y., et al. (2015). A human interactome in three quantitative dimensions organized by stoichiometries and abundances. Cell 163(3), 712-723. doi: 10.1016/j.cell.2015.09.053.

Hines, M.E., 2nd, et al. (2007). Efficacy of spheroplastic and cell-wall competent vaccines for *Mycobacterium avium* subsp. *paratuberculosis* in experimentally-challenged baby goats. Vet Microbiol 120(3-4), 261-283. doi: 10.1016/j.vetmic.2006.10.030.

Hines, M.E., 2nd, et al. (2014). Evaluation of novel oral vaccine candidates and validation of a caprine model of Johne's disease. Front Cell Infect Microbiol 4, 26. doi: 10.3389/fcimb.2014.00026.

Janji, B., et al. (2010). The actin filament cross-linker L-plastin confers resistance to TNF-alpha in MCF-7 breast cancer cells in a phosphorylation-dependent manner. J Cell Mol Med 14(6A), 1264-1275. doi: 10.1111/.1582-4934.2009.00918.x.

Jurado, J.O., et al. (2012). IL-17 and IFN-gamma expression in lymphocytes from patients with active tuberculosis correlates with the severity of the disease. J Leukoc Biol 91(6), 991-1002. doi: 10.1189/jlb.1211619.

Ehlers, S., et al. (1999). NOS2-derived nitric oxide regulates the size, quantity and quality of granuloma formation in *Mycobacterium avium*-infected mice without affecting bacterial loads. Immunology 98(3), 313-323.

Li L, et al. 2005. The complete genome sequence of *Mycobacterium avium* subspecies *paratuberculosis*. Proceedings of the National Academy of Sciences of the United States of America 102:12344-12349.

Li, L., et al. (2017). Early detection of *Mycobacterium avium* subsp. *paratuberculosis* infection in cattle with multiplex-bead based immunoassays. PLoS One 12(12), e0189783. doi: 10.1371/journal.pone.0189783.

In, J., et al. (2015). Transcriptome analysis of the mammary gland from GH transgenic goats during involution. Gene 665(2), 228-234. doi: 10.1016/j.gene.2015.04.017.

Linnabary RD, et al. 2001. Johne's disease in Cattle. Council for Agricultural Science and Technology 17:1-10.

Losinger WC. 2005. Economic impact of reduced milk production associated with Johne's disease on dairy operations in the USA. J.Dairy Res. 72:425-432.

Love, M.I., et al. (2014). Moderated estimation of fold change and dispersion for RNA-seq data with DESeq2. Genome Biol 15(12), 550. doi: 10.1186/s13059-014-0550-8.

Magombedze, G., et al. (2014). Competition for antigen between Th1 and Th2 responses determines the timing of the immune response switch during *Mycobaterium avium* subspecies *paratuberulosis* infection in ruminants. PLoS Comput Biol 10(1), e1003414. doi: 10.1371/journal.pcbi.1003414.

Marteau, J.B., et al. (2005). Collection and storage of human blood cells for mRNA expression profiling: a 15-month stability study. Clin Chem 51(7), 1250-1252. doi: 10.1373/clinchem.2005.048546.

McKenna, S.L., et al. (2005). Comparison of two enzyme-linked immunosorbent assays for diagnosis of *Mycobacterium avium* subsp. *paratuberculosis*. J Vet Diagn Invest 17(5), 463-466. doi: 10.1177/104063870501700510.

NCBI (2016). NCBI Capra hircus Annotation Release 102 [Online]. Available: https://www.ncbi.nlm.nih.gov/genome/annotation_euk/Capra_hircus/102/ [Accessed].

Nicola, N.A., et al. (2015). Leukemia inhibitory factor (LIF). Cytokine Growth Factor Rev 26(5), 533-544. doi: 10.1016/j.cytogfr.2015.07.001.

Novick, D., et al. (1999). Interleukin-18 binding protein: a novel modulator of the Th1 cytokine response. Immunity 10(1), 127-136.

Ott, S.L., et al. (1999). Herd-level economic losses associated with Johne's disease on US dairy operations. Preventive veterinary medicine 40(3-4), 179-192.

Park ST, et al. 2008. Regulation of the SigH stress response regulon by an essential protein kinase in *Mycobacterium tuberculosis*. Proceedings of the National Academy of Sciences U.S.A. 105:13105-13110.

Schlecht, U., et al. (2012). Multiplex assay for condition-dependent changes in protein-protein interactions. Proc Natl Acad Sci U S A 109(23), 9213-9218. doi: 10.1073/pnas.1204952109.

Seto, S., et al. (2012). Coronin-1a inhibits autophagosome formation around *Mycobacterium tuberculosis*-containing phagosomes and assists mycobacterial survival in macrophages. Cell Microbiol 14(5), 710-727. doi: 10.1111/1.1462-5822.2012.01754.x.

Shippy, D.C., et al. (2017). Superior protection from live-attenuated vaccines directed against Johne's disease. Clin Vaccine Immunol 24(1). doi: 10.1128/CVI.00478-16.

Sockett, D.C., et al. (1992). Evaluation of conventional and radiometric fecal culture and a commercial DNA probe for diagnosis of *Mycobacterium paratuberculosis* infections in cattle. Can J Vet Res 56(2), 148-153.

Souza, C., et al. (2013). Mannosylated lipoarabinomannans from *Mycobacterium avium* subsp. *paratuberculosis* alters the inflammatory response by bovine macrophages and suppresses killing of

(56) References Cited

OTHER PUBLICATIONS

*Mycobacterium avium* subsp. *avium* organisms. PLoS One 8(9), e75924. doi: 10.1371/journal.pone.0075924.

Stabel, J.R. (2000). Cytokine secretion by peripheral blood mononuclear cells from cows infected with *Mycobacterium paratuberculosis*. American Journal of Veterinary Research 61(7), 754-760.

Stabel, J.R., et al. (2009). Pathogenesis of *Mycobacterium avium* subsp. *paratuberculosis* in neonatal calves after oral or intraperitoneal experimental infection. Veterinary Microbiology 136(3-4), 306-313.

Sweeney, R.W., et al. (1998). Interferon-gamma and interleukin 4 gene expression in cows infected with *Mycobacterium paratuberculosis*. American Journal of Veterinary Research 59(7), 842-847.

Szklarczyk, D., et al. (2015). STRING v10: protein-protein interaction networks, integrated over the tree of life. Nucleic Acids Res 43(Database issue), D447-452. doi: 10.1093/nar/gku1003.

\* cited by examiner

A.

B.

A

B

BIOMARKERS FOR EARLY DIAGNOSIS AND DIFFERENTIATION OF MYCOBACTERIAL INFECTION

CROSS-REFERENCE TO RELATED APPLICATIONS

This application claims priority to U.S. Provisional Patent Application No. 62/728,387 filed Sep. 7, 2018, which is incorporated herein in its entirety.

STATEMENT REGARDING FEDERALLY SPONSORED RESEARCH

This invention was made with government support under 2013-67015-21347, 2018-67015-28243 and 2016-33610-25438 awarded by the USDA/NIFA. The government has certain rights in the invention.

REFERENCE TO A SEQUENCE LISTING SUBMITTED VIA EFS-WEB

The content of the ASCII text file of the sequence listing named "960296_02450_ST25.txt" which is 21.4 kb in size was created on Aug. 28, 2019 and electronically submitted via EFS-Web herewith the application is incorporated herein by reference in its entirety.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BACKGROUND OF THE INVENTION

The field of the invention is vaccine and diagnostic biomarkers. More particularly, the invention relates to a set of biomarkers for diagnosing mycobacterial infection and distinguishing between vaccinated and infected animals.

Mycobacterial infections cause significant health problems to humans and animals including human tuberculosis, bovine tuberculosis, and Johne's disease. Johne's disease (aka *paratuberculosis*) is caused by infection with *Mycobacterium avium* subspecies *paratuberculosis* (*M. ap*); this disease causes severe economic losses estimated at $500 million per year for the US dairy industry alone, and these infections constitute a problem for 91% of dairy herds. Bovine tuberculosis, which is caused by infection with *M. bovis*, is endemic in dairy herds in several parts of the developing world and a significant problem for the wildlife animals in several developed countries (e.g., UK, USA, and Australia).

Current diagnostics can detect mycobacterial infections in cattle that have started to shed the bacteria or developed an antibody response. The available diagnostic tools are unreliable to detect early stages of infection or to differentiate infected from vaccinated animals (aka the DIVA principle). Early detection of mycobacterial infections is imperative to control the infection in herds. Further, the availability of a DIVA-based assay will facilitate adoption of new vaccines that can prevent *M. ap* infection.

Needed in the art are methods or diagnostic tools for detecting early stages of mycobacterial infection. Additionally, needed in the art are methods or diagnostic tools for distinguishing vaccinated from infected animals.

SUMMARY OF THE INVENTION

The present invention overcomes the aforementioned drawbacks by providing a set of biomarkers to diagnose infected animals and distinguishing between vaccinated and infected animals.

In a first aspect, provided herein is a method for diagnosis of mycobacterial infection in a mammal, the method comprising the steps of a) obtaining a first type of sample from the mammal; b) measuring the expression level in the sample of at least one biomarker selected from the group consisting of LOC108634521, LOC108637251, LOC108637252, LOC108634594, FAM198B, LOC108637671, CDCP1, TMTC1, BAIAP2L1, MEI1, SEPT10, IFNG, IL17F, FCER2, ADGRG1, APBB1, PIWIL2, AOAH, and homologs thereof and comparing the level of the biomarker against the level detected in a first type of sample from an uninfected mammal of the same species; and c) determining the infection status of the mammal, wherein differential expression of the biomarker is indicative of a mycobacterial infection in the mammal. In some embodiments, the method is used for early diagnosis and detection of mycobacterial infection in a mammal. In some embodiments, the measuring is via ELISA assay for antibodies formed against the biomarker. In some embodiments, measuring is via quantitative PCR. In some embodiments, the sample is a blood sample. In some embodiments, the mammal is selected from the group consisting of cow, sheep and goat.

In a second aspect, provided herein is a method for differentiating between mammals who have been vaccinated with a live-attenuated mycobacterial vaccine and non-vaccinated mammals, the method comprising the steps of a) obtaining a first type of sample from the mammal; b) measuring the expression level in the sample of at least one biomarker selected from the group consisting of LOC108634521, NOS2, LOC108637251, TINAGL1, RETN, C1QL2, TDRD10, TGFB3, ADGRE2, LIPG, KCNJ2, AQP9, BPI, IL9, IL1R2, IL36B, IGF1, BGN, PIWIL2, RAET1E, CRABP2, AOAH, and homologs thereof and comparing the level of the biomarker against the level detected in a first type of sample from a non-vaccinated mammal of the same species; and c) determining the vaccination status of the mammal, wherein differential expression of the biomarker is indicative of a mammal who has been vaccinated with a live-attenuated mycobacterial vaccine. In some embodiments, the measuring is via ELISA assay for antibodies formed against the biomarker. In some embodiments, the measuring is via quantitative PCR. In some embodiment, the sample is a blood sample. In some embodiments, the mammal is selected from the group consisting of cow, sheep and goat.

In some embodiments, the live-attenuated mycobacterial vaccine is a *mycobacterium* mutant vaccine. In some embodiments, the *mycobacterium* mutant vaccine comprises at least one mutation in at least one gene sequence encoding global gene regulators (GGRs) selected from the group consisting of sigH, sigL and LipN.

In a third aspect, provided herein is a method for differentiating between mammals who have been vaccinated with a live-attenuated mycobacterial vaccine and infected mammals, the method comprising the steps of a) obtaining a first type of sample from the mammal; b) measuring the expression level in the sample of at least one biomarker selected from the group consisting of LOC106503226, PMP22, ART5, LOC102169116, GNLY, ASAP3, LOC108633178, TBKBP1, SLC17A7, LOC108638192, IFNG and homologs thereof and comparing the level of the biomarker against the level detected in a first type of sample from an infected mammal of the same species; and c) determining the vaccination status of the mammal, wherein differential expression of the biomarker is indicative of a mammal who has been vaccinated with a live-attenuated mycobacterial vaccine. In some embodiments, the measuring is via ELISA assay for antibodies formed against the biomarker. In some embodiments, the measuring is via quantitative PCR. In some embodiments, the sample is a blood sample. In some embodiments, the mammal is selected from the group consisting of cow, sheep and goat.

In some embodiments, the live-attenuated mycobacterial vaccine is a *mycobacterium* mutant vaccine. In some embodiments, the *mycobacterium* mutant vaccine comprises at least one mutation in at least one gene sequence encoding global gene regulators (GGRs) selected from the group consisting of sigH, sigL and LipN.

In a fourth aspect, provided herein is a method for differentiating between mammals who have been vaccinated with a live-attenuated mycobacterial vaccine, non-vaccinated naïve mammals, and infected mammals, the method comprising the steps of obtaining a first type of sample from the mammal; measuring the expression level of FAM198B and AOAH in the sample; determining the vaccination or infection status of the mammal, wherein when relative expression of FAM198B is higher than AOAH the subject is infected, when relative expression of AOAH is higher than FAM198B the subject is vaccinated, and when the relative expression of AOAH and FAM198B are equal the subject is naïve.

In some embodiments, the measuring is via ELISA assay for antibodies formed against the biomarker. In some embodiments, the measuring is via quantitative PCR. In some embodiments, the sample is a blood sample. In some embodiments, the mammal is selected from the group consisting of cow, sheep, and goat. In some embodiments, the live-attenuated mycobacterial vaccine is a *mycobacterium* mutant vaccine. In some embodiments, the *mycobacterium* mutant vaccine comprises at least one mutation in at least one gene sequence encoding global gene regulators (GGRs) selected from the group consisting of sigH, sigL and LipN.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, reference is made therefore to the claims and herein for interpreting the scope of the invention.

BRIEF DESCRIPTION OF THE DRAWINGS

The patent or application file contains at least one drawing in color. Copies of this patent or patent application publication with color drawings will be provided by the Office upon request and payment of the necessary fee.

DETAILED DESCRIPTION OF THE INVENTION

Figure 1:
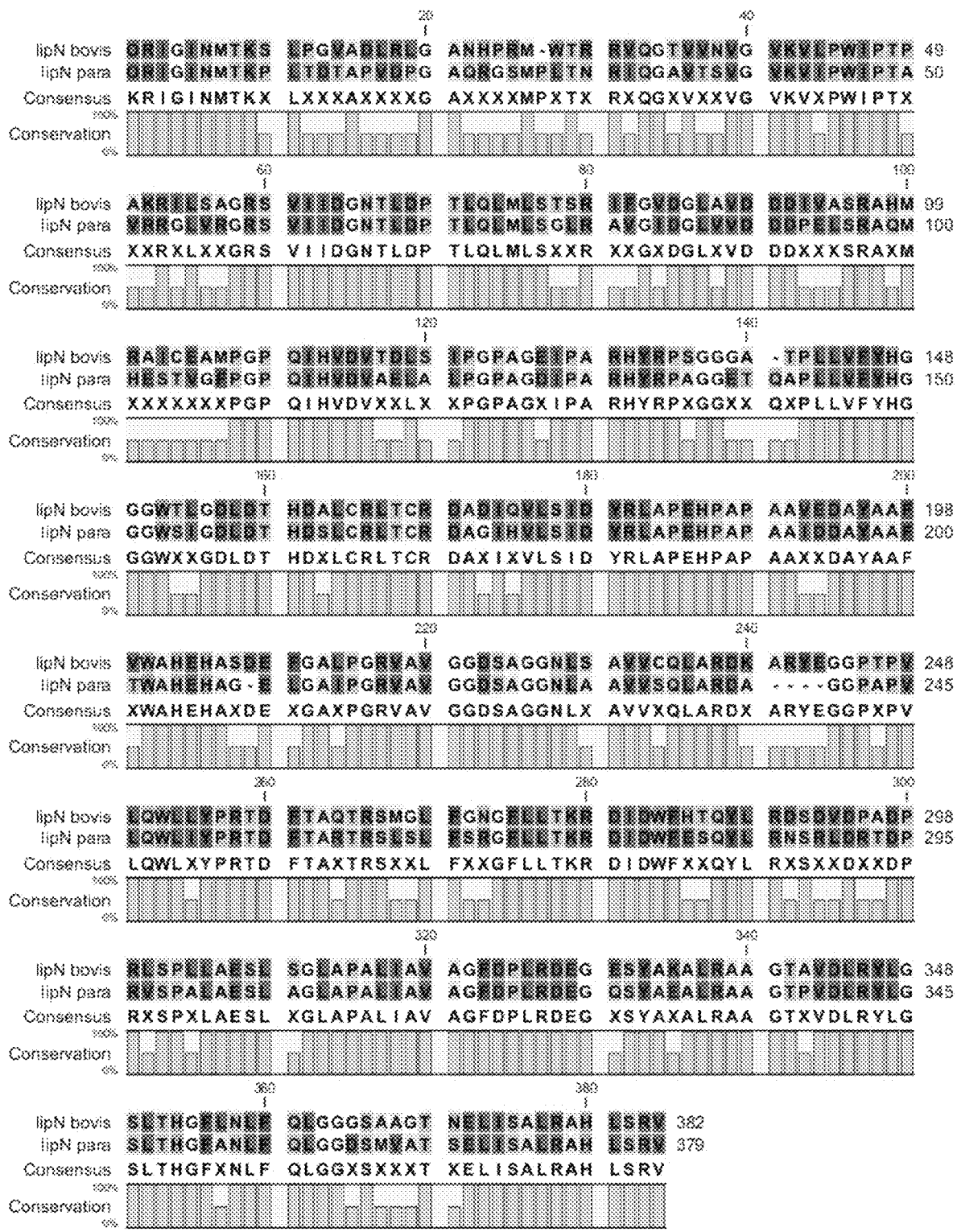
FIG. 1 is a graph showing the alignment plot of amino acids deduced from the protein sequence in LipN of both *M. paratuberculosis* (SEQ ID NO:1) and *M. bovis* (SEQ ID NO:2). The consensus sequence is SEQ ID NO:3. Peptides conserved in *M. paratuberculosis* sequence but absent from *M. bovis* were targets for previous DIVA testing methods.
Figure 2A:
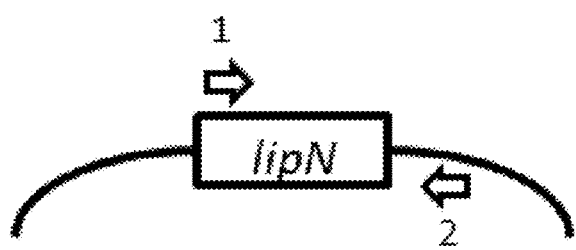
FIGS. 2A-2B is a diagram showing multiplex PCR strategy using 3 primers. (A) Wild-type (virulent) strain with intact lipN gene. (B) LAV strain with scar sequence from hygromycin cassette removal represented by the black rectangle.
Figure 2B:
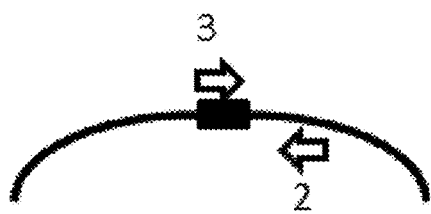

The term "*mycobacterium*," as used herein, refers to a genus of actinobacteria given its own family, the mycobacteriaceae. The genus includes pathogens known to cause serious diseases in mammals, including tuberculosis (*Mycobacterium tuberculosis*) and leprosy (*Mycobacterium leprae*).

*Mycobacterium tuberculosis* complex (MTBC) members are causative agents of human and animal tuberculosis. Species in this complex may include *M. tuberculosis*, the major cause of human tuberculosis, *M. bovis, M. bovis* BCG, *M. africanum, M. canetti, M. caprae, M. microti*, and *M. pinnipedii*.

*Mycobacterium avium* complex (MAC) is a group of species that, in a disseminated infection but not lung infection, used to be a significant cause of death in AIDS patients. Species in this complex include *M. avium, M. avium paratuberculosis*, which has been implicated in Crohn's disease in humans and is the causative agent of Johne's disease in cattle and sheep, *M. avium silvaticum, M. avium "hominissuis," M. colombiense*, and *M. indicus pranii*.

Mycobacterial infections are notoriously difficult to treat. The organisms are hardy due to their cell wall, which is neither truly Gram negative nor Gram positive. In addition, they are naturally resistant to a number of antibiotics that disrupt cell-wall biosynthesis, such as penicillin. Due to their unique cell wall, they can survive long exposure to acids, alkalis, detergents, oxidative bursts, lysis by complement, and many antibiotics. Most mycobacteria are susceptible to the antibiotics clarithromycin and rifamycin, but antibiotic-resistant strains have emerged.

The term "biomolecule," as used herein, refers to any organic molecule that is part of or from a living organism. Biomolecules may include nucleic acids, a nucleotide, a polynucleotide, an oligonucleotide, a peptide, a protein, a carbohydrate, a ligand, a receptor, among others. In one embodiment of the present invention, biomolecules may include genes and their expression products.

The term "expression product," as used herein, refers to any product produced during the process of gene expression. These products are often proteins, but in non-protein coding genes such as ribosomal RNA (rRNA), transfer RNA (tRNA) or small nuclear RNA (snRNA) genes, the product is a functional RNA.

The terms "polypeptide," "peptide," and "protein," as used herein, refer to a polymer comprising amino acid residues predominantly bound together by covalent amide bonds. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

The term "recombinant protein," as used herein, refers to a polypeptide of the present disclosure which is produced by recombinant DNA techniques, wherein generally, DNA encoding a polypeptide is inserted into a suitable expression vector which is in turn used to transform a heterologous host cell (e.g., a microorganism or yeast cell) to produce the heterologous protein.

The term "recombinant nucleic acid" or "recombinant DNA," as used herein, refers to a nucleic acid or DNA of the present disclosure which is produced by recombinant DNA techniques, wherein generally, DNA encoding a polypeptide is inserted into a suitable expression vector which is in turn used to transform a host cell to produce the heterologous protein.

The term "mammal," as used herein, refers to any living species which can be identified by the presence of sweat glands, including those that are specialized to produce milk to nourish their young. In one embodiment, the mammal suitable for the present invention may include bubaline, elephantine, musteline, pardine, phocine, rhinocerine, caprine, hircine, leonine, leporine, lupine, lyncine, murine, rusine, tigrine, ursine, vulpine, zebrine, vespertilionine, porcine, bovine, equine, swine, elaphine, ovine, caprine, camelidae, feline, cervine, primate, human and canine mammals. In one preferred embodiment of the present invention, the mammal may be one of the ruminants such as cattle, goats, sheep, giraffes, yaks, deer, camels, llamas, antelope, and some macropods. In one specific embodiment of the present invention, the mammal may include any of the milk cattle species, such as cow, sheep and goat.

The term "antibody," as used herein, refers to a class of proteins that are generally known as immunoglobulins. The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

The term "marker" or "biomarker," as used herein, refers to a biomolecule (e.g., protein, nucleic acid, carbohydrate, or lipid) that is differentially expressed in the cell, differentially expressed on the surface of an infected cell, differentially phosphorylated, or differentially secreted by a infected cell in comparison to a normal cell or in a paracrine fashion by neighboring uninfected cells, and which is useful for the diagnosis of mycobacterial infection, differentiating between infected and vaccinated animals, and for preferential targeting of a pharmacological agent to an infected mammal. In some embodiments, the biomarker is differentially expressed in an infected subject in comparison to a normal subject. In some embodiments, the biomarker is differentially expressed in a vaccinated subject in comparison to a non-vaccinated subject. In some embodiments, the biomarker is differentially expressed in a vaccinated subject in comparison to an infected subject.

The term "differentially expressed," as used herein, refers to a change in expression of at least 2-fold. In some embodiments, differential expression indicates that a given biomarker is over-expressed in a first subject or cell in comparison to a second subject or cell, for instance, at least 2-fold over-expression, at least 3-fold over-expression, at least 4-fold over-expression or more in comparison to the second subject or cell. In some embodiments, differential expression indicates that a given biomarker has decreased expression in a first subject or cell in comparison to a second subject or cell, for instance, at least a 2-fold decease in expression, at least a 3-fold decrease in expression, at least a 4-fold decrease in expression or more.

The term "mycobacterial-specific biomarkers," as used herein, refers to biomarkers which are specifically related to mycobacterial infection. Some of these biomarkers are listed in FIG. 1 and Tables 4 and 5.

The term "lyophilization," as used herein, refers to freezing of a material at low temperature followed by dehydration by sublimation, usually under a high vacuum. Lyophilization is also known as freeze drying. Many techniques of freezing are known in the art of lyophilization such as tray freezing, shelf freezing, spray-freezing, shell-freezing and liquid nitrogen immersion. Each technique will result in a different rate of freezing. Shell freezing may be automated or manual. For example, flasks can be automatically rotated by motor driven rollers in a refrigerated bath containing alcohol, acetone, liquid nitrogen, or any other appropriate fluid. A thin coating of product is evenly frozen around the inside "shell" of a flask, permitting a greater volume of material to be safely processed during each freeze drying run. Tray freezing may be performed by, for example, placing the samples in lyophilizer, equilibrating 1 hr at a shelf temperature of 0° C., then cooling the shelves at 0.5° C./min to −40° C. Spray-freezing, for example, may be performed by spray freezing into liquid, dropping by ~20 μl droplets into liquid $N_2$, spray freezing into vapor over liquid, or by other techniques known in the art.

The term "antigen," as used herein, refers to any molecule that is capable of eliciting an immune response, whether a cell-mediated or humoral immune response, whether in the presence or absence of an adjuvant. An antigen can be any type of molecule, e.g., a peptide or protein, a nucleic acid, a carbohydrate, a lipid, and combinations thereof. A "vaccine antigen" is an antigen that can be used in a vaccine preparation. A "therapeutic antigen" is an antigen that can be used for therapeutic purposes.

The term "vaccine," as used herein, refers to an antigenic preparation used to produce active immunity to a disease, in order to prevent or ameliorate the effects of infection. The antigenic moiety making up the vaccine may be either a live or killed microorganism, or a natural product purified from a microorganism or other cell including, but not limited to tumor cells, a synthetic product, a genetically engineered protein, peptide, polysaccharide or similar product or an allergen.

The term "immunologically active," as used herein, refers to the ability to raise one or more of a humoral response or a cell mediated response specific to an antigen.

The term "adjuvant," as used herein, refer to compounds that, when used in combination with specific vaccine antigens in formulations, augment or otherwise alter or modify the resultant immune responses. An adjuvant combined with a vaccine antigen increases the immune response to the vaccine antigen over that induced by the vaccine antigen alone. An adjuvant may augment humoral immune responses or cell-mediated immune responses or both humoral and cell-mediated immune responses against vaccine antigens.

The term "detecting," as used herein, refers to confirming the presence of the biomarker or marker present in the sample. Quantifying the amount of the biomarker or marker present in a sample may include determining the concentration of the biomarker present in the sample. Detecting and/or quantifying may be performed directly on the sample, or indirectly on an extract therefrom, or on a dilution thereof.

The term "homology," as used herein, refers to the resemblance or similarity between two nucleotide or amino acid sequences. As applied to a gene, "homolog" may refer to a gene similar in structure and/or evolutionary origin to a gene in another organism or another species. As applied to nucleic acid molecules, the term "homolog" means that two nucleic acid sequences, when optimally aligned (see below), share at least 80 percent sequence homology, preferably at least 90 percent sequence homology, more preferably at least 95, 96, 97, 98 or 99 percent sequence homology. "Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides that are not identical but differ by redundant nucleotide substitutions (the nucleotide substitution does not change the amino acid encoded by the particular codon). For example, "95% nucleotide homology" refers to a comparison of the nucleotides of two nucleic acid molecules which, when optimally aligned, have 95% nucleotide homology.

In one aspect, the present invention relates to a method for diagnosis of mycobacterial infection in a mammal. In one embodiment, the present invention discloses a method for early detection of mycobacterial infection. The term "early detection," as used herein, refers to detection of mycobacterial infection during the early stage of infection, e.g., a stage before the development of chronic diarrhea.

In another embodiment, the present invention discloses a method for differentiating a vaccinated mammal from a non-infected mammal or a mycobacterial infected mammal.

The detection of mycobacterial infection and related diseases such as Johne's disease is very difficult because the disease generally takes many years to develop, and the organism is shed by the mammal periodically, so every mammal must be repeatedly tested over long time periods.

Applicants have identified mycobacterial-specific biomarkers and host-specific biomarkers, such as genes and/or expression products derived thereof, useful for detection of mycobacterial infection. Mycobacterial-specific biomarkers, host-specific biomarkers or a combination of such biomarkers may also be used to differentiate a vaccinated mammal (e.g., from genetically engineered vaccines) from a non-infected mammal or a mycobacterial-infected mammal.

Differentiating Vaccinated Mammals from Mycobacterial-Infected Mammals

In one embodiment, the present invention discloses a method for differentiating a vaccinated mammal from a mycobacterial infected mammal.

In one embodiment, the method for differentiating a vaccinated mammal from a mycobacterial-infected mammal comprises the steps of (a) obtaining a sample from the mammal; (b) testing the sample for the concentration level of at least one biomarker and comparing the level of the biomarker against the level detected in an infected mammalian sample; and (c) determining the infection or vaccination status of the mammal.

A sample suitable for the present invention may include any biological sample from the mammal. The biological sample may include, without limitation, saliva, sputum, blood, plasma, serum, urine, feces, cerebrospinal fluid, amniotic fluid, wound exudate, or tissue of the subject of mammal. In one specific embodiment, the biological sample is a blood sample. In some embodiments, when comparing the expression level of a biomarker between two subjects, it is desirable to compare expression levels in the same type of sample.

A major problem in employing mass vaccination program for the control of Johne's disease in dairy herds is the inability to differentiate between infected and vaccinated animals with the current vaccine (DIVA principal). Applicants have previously proposed using genetically engineered vaccines (PCT patent application publication WO2014164055, U.S. Pat. Nos. 9,663,758, and 9,446,110, each of which is incorporated herein by reference). One would wish to consider the DIVA principal and wish to distinguish between *M. paratuberculosis* infected and Johne's disease vaccinated animals that have been vaccinated with genetically engineered vaccines.

In one embodiment, Applicants identify biomolecules as mycobacterial-specific biomarkers. For example, the biomolecules of mycobacterial-specific biomarkers may include genes and their expression products which are present in a *M. ap* wild-type strain but not present or have a low expression level in genetically engineered vaccines and vaccinated animals. In one embodiment involving sigL and sigH mutants, the mycobacterial-specific biomarker may comprise at least one member selected from the group consisting of gene sequences Q73SF4, Q73Y73, Q73ZE6, Q73SL7, Q73VK6, Q73XZ0, Q740D1 and Q73UE0 and expression products derived thereof. In another embodiment, the mycobacterial-specific biomarker may comprise at least two, three, four, five, six, seven or eight members selected from the group consisting of gene sequences Q73SF4, Q73Y73, Q73ZE6, Q73SL7, Q73VK6, Q73XZ0, Q740D1 and Q73UE0 and expression products derived thereof. Preferably, the mycobacterial-specific biomarker may comprise at least two members selected from the group as discussed above.

In one embodiment involving sigL and sigH mutants, the mycobacterial-specific biomarker comprises at least one member selected from the group consisting of gene sequences Q73VL6, Q73YW9, Q741L4, Q744E5, Q73YP5, Q73WE5, Q73U21, Q73UH9, Q741M5, Q742F4, and Q73SU6 and expression products derived thereof. In one embodiment, the mycobacterial-specific biomarker comprises at least two, three, four, five, six, seven, eight, nine or ten members selected from the group consisting of gene sequences Q73VL6, Q73YW9, Q741L4, Q744E5, Q73YP5, Q73WE5, Q73U21, Q73UH9, Q741M5, Q742F4, and Q73SU6 and expression products derived thereof.

Applicants envision that the present invention may be applicable to any genetically engineered vaccines. In some embodiments, the vaccine may be an inactived vaccine (e.g., Mycopar™). In one specific embodiment, the present invention is applicable to live attenuated vaccines. The example of the live attenuated vaccines may include sigL, sigH, or LipN mutants. PCT patent application publication WO20141640055A1 discloses live attenuated vaccines, such as sigL and sigH mutants. PCT patent application publication WO20141640055A1 is incorporated herein by reference in its entirety.

In one embodiment, the presence or absence of the biomarkers in a mammal may demonstrate the infection status of the mammal. In one specific embodiment, the biomarkers that are significantly over-expressed in the wild type strain and not in the mutant vaccine and could be used for the mutant vaccine-DIVA testing.

For example, when the biomarkers are those significantly over-expressed in the wild type strain and not in the mutant vaccine, the presence of at least one biomarker in a mammal shows that the mammal may be infected and not merely vaccinated. On the other hand, the absence of at least one biomarker in a mammal shows that the mammal may be vaccinated.

In one embodiment, Applicants envision that the present invention is also applicable when antigens are inoculated to a mammal and the infection status of the mammal needs to be identified. Specifically, the infection status may include whether a mammal is vaccinated or whether a mammal is infected with *M. paratuberculosis*.

Table 7, which tabulates the result of one of the Examples drawn to host transcriptome analysis of goats, lists additional markers that will be useful for embodiments of the invention. The first part of Table 7 lists DNA markers that are useful for early diagnosis of John's disease in ruminants, as described above, because the markers differentiate infected from naïve animals. Table 7 lists the locus in goats and provides homologous locus in cows, if it is known. Table 7 also lists host markers that can differentiate live attenuated vaccine (LAV) vaccinated animals from naïve animals and markers that can differentiate inactivated-vaccine immunized from naïve animals. Table 7 also lists host markers to distinguish between infected and vaccinated animals.

As used herein, "naïve" refers to animals that are not vaccinated nor infected.

In addition to the biomarkers recited herein, additional biomarkers useful in the disclosed methods include those described in U.S. Pat. No. 10,054,586, which is incorporated herein in its entirety.

In some embodiments, the present invention provides methods of distinguishing between infected and naïve animals by measuring expression of one or more biomarkers selected from the group of LOC108634521, LOC108637251, LOC108637252, LOC108634594, FAM198B, LOC108637671, CDCP1, TMTC1, BAIAP2L1, MEI1, SEPT10, IFNG, IL17F, FCER2, ADGRG1, APBB1, PIWIL2, AOAH, and homologs thereof (Table 1) In some embodiments, two, three, four, five, six or more of the recited biomarkers may be measured.

In some embodiments, the present invention provides methods of distinguishing between live attenuated vaccine (LAV) vaccinated animals from naïve animals by measuring expression of one or more biomarker selected from the group of LOC108634521, NOS2, LOC108637251, TINAGL1, RETN, C1QL2, TDRD10, TGFB3, ADGRE2, LIPG, KCNJ2, AQP9, BPI, IL9, IL1R2, IL36B, IGF1, BGN, PIWIL2, RAET1E, CRABP2, AOAH, and homologs thereof (Table 2) In some embodiments, two, three, four, five, six or more of the recited biomarkers may be measured.

In some embodiments, the present invention provides methods of distinguishing between LAV-vaccinated animals from infected animals by measuring expression of one or more biomarker selected from the group of LOC106503226, PMP22, ART5, LOC102169116, GNLY, ASAP3, LOC108633178, TBKBP1, SLC17A7 and homologs thereof (Table 3) In some embodiments, two, three, four, five, six or more of the recited biomarkers may be measured.

In some embodiments, biomarkers may be used to distinguish between naïve, infected, and vaccinated animals. By measuring expression of two or more biomarkers recited herein, an animal may be identified as naïve, infected, or vaccinated. A selection of suitable biomarkers and their relative expression is outlined in Table 4A and Table 4B. For example, as demonstrated in Table 4A, when relative expression of FAM198B is higher than relative expression of AOAH, the subject is infected with a mycobacterial infection. When relative expression of AOAH is higher than relative expression of FAM198B, the subject has been vaccinated with an LAV vaccine. When relative expression of AOAH and FAM198B are equal, or within error of the method used to quantify relative expression, the subject is naïve. Similar comparisons and conclusions may be drawn using other biomarkers described herein, such as those outlined in Table 4B or any of Tables 1-3.

TABLE 1

List of host (goat and cow) genes that can differentiation infected from naïve animals.

| Symbol | Entrez Gene ID | Description | Expression in a Naïve Animal | Expression in an Infected Animal | Log$_2$ Fold Change in Expression Infected vs Naïve |
|---|---|---|---|---|---|
| LOC108634521 | 108634521 | non-coding RNA | 0.66 | 258.7 | 8.66 |
| LOC108637251 | 108637251 | multidrug resistance-associated protein 4-like | 1.28 | 137.44 | 6.74 |
| LOC108637252 | 108637252 | multidrug resistance-associated protein 4-like | 5.31 | 90.39 | 4.11 |
| LOC108634594 | 108634594 | multidrug resistance-associated protein 4-like | 3.35 | 110.84 | 5.06 |
| FAM198B | 102191727 | family with sequence similarity 198 member B | 71.81 | 768.85 | 3.42 |
| LOC108637671 | 108637671 | tripartite motif-containing protein 5-like | 46.57 | 316.63 | 2.77 |
| CDCP1 | 102187276 | CUB domain containing protein | 8.9 | 36.66 | 2.02 |
| TMTC1 | 102185637 | transmembrane and tetratricopeptide repeat | 13.2 | 47.85 | 1.86 |
| BAIAP2L1 | 102173150 | BAI1 associated protein 2 like | 8.17 | 29.54 | 1.85 |
| MEI1 | 102169168 | meiotic double-stranded break formation protein | 203.8 | 609.18 | 1.58 |
| SEPT10 | 102171885 | septin 10 | 16.83 | 40.16 | 1.27 |
| IFNG | 100860815 | interferon gamma | 63.77 | 19.26 | −1.75 |
| IL17F | 102171111 | interleukin 17F | 625.76 | 267.69 | −1.22 |
| FCER2 | 102171507 | Fc fragment of IgE receptor II | 626.49 | 243.68 | −1.36 |
| ADGRG1 | 102171366 | G protein-coupled receptor G | 72.43 | 21.2 | −1.78 |
| APBB1 | 102179305 | amyloid beta precursor protein binding family B member | 97.39 | 21.75 | −2.16 |
| PIWIL2 | 102173845 | piwi like RNA-mediated gene silencing | 57.32 | 10.67 | −2.41 |
| AOAH | 102189546 | acyloxyacyl hydrolase | 258.05 | 268.21 | 0.06 |

TABLE 2

List of host (goat and cow) genes that can differentiate LAV vaccinated from naïve animals.

| Symbol | Entrez Gene ID | Description | Expression in a Naïve Animal | Expression in an LAV vaccinated Animal | Log$_2$ Fold Change in Expression Vaccinated vs Naïve |
|---|---|---|---|---|---|
| LOC108634521 | 108634521 | non-coding RNA | 0.66 | 238.29 | 8.54 |
| NOS2 | 100860742 | nitric oxide synthase 2 | 0.78 | 103.4 | 7.03 |
| LOC108637251 | 108637251 | multidrug resistance-associated protein 4-like | 1.28 | 150.28 | 6.87 |
| TINAGL1 | 102169636 | tubulointerstitial nephritis antigen like | 4.62 | 90.01 | 4.27 |
| RETN | 102170965 | resistin | 44.98 | 708.35 | 3.96 |
| C1QL2 | 102176742 | complement C1q like 2 | 2.29 | 30.2 | 3.69 |
| TDRD10 | 102174259 | tudor domain containing 10 | 0 | 2.49 | 3.53 |
| TGFB3 | 102189962 | transforming growth factor beta 3 | 40.44 | 367.3 | 3.19 |
| ADGRE2 | 102171592 | adhesion G protein-coupled receptor E2 | 101.97 | 601.2 | 2.56 |
| LIPG | 102191574 | lipase G endothelial type | 33.18 | 175.34 | 2.40 |
| KCNJ2 | 102168940 | potassium voltage-gated channel subfamily J member 2 | 78.28 | 378.07 | 2.27 |
| AQP9 | 102181396 | aquaporin 9 | 72.94 | 342.39 | 2.24 |
| BPI | 102185756 | bactericidal/permeability-increasing protein | 13.67 | 49.85 | 1.85 |
| IL9 | 102179848 | interleukin 9 | 13.72 | 4.82 | −1.54 |
| IL1R2 | 102186601 | interleukin 1 receptor type 2 | 170.86 | 47.04 | −1.86 |
| IL36B | 102182235 | interleukin 36 beta | 80.82 | 14.69 | −2.45 |
| IGF1 | 100860838 | insulin like growth factor | 109.36 | 19.9 | −2.45 |
| BGN | 102183219 | biglycan | 227.52 | 26.44 | −3.10 |
| PIWIL2 | 102173845 | piwi like RNA-mediated gene silencing | 57.32 | 7 | −3.10 |
| RAET1E | 108636743 | retinoic acid early transcript | 832.23 | 48.24 | −4.11 |
| CRABP2 | 102174348 | cellular retinoic acid binding protein 2 | 103.46 | 3.31 | −4.91 |
| AOAH | 102189546 | acyloxyacyl hydrolase | 258.05 | 1014.3 | 1.98 |

TABLE 3

List of host (goat and cow) genes that can differentiate LAV vaccinated from infected animals.

| Symbol | Entrez Gene ID | Description | Expression in an Infected Animal | Expression in an LAV vaccinated Animal | Log$_2$ Fold Change in Expression Infected vs Vaccinated |
|---|---|---|---|---|---|
| LOC106503226 | 106503226 | non-coding RNA | 37.38 | 5.83 | 2.74 |
| PMP22 | 102184371 | peripheral myelin protein 22 | 268.96 | 36.55 | 2.87 |
| ART5 | 102169686 | ADP-ribosyltransferase 5 | 16.98 | 103.7 | −2.62 |
| LOC102169116 | 102169116 | ecto-ADP-ribosyltransferase 5 | 43.11 | 198.79 | −2.20 |

TABLE 3-continued

List of host (goat and cow) genes that can differentiate LAV vaccinated from infected animals.

| Symbol | Entrez Gene ID | Description | Expression in an Infected Animal | Expression in an LAV vaccinated Animal | Log$_2$ Fold Change in Expression Infected vs Vaccinated |
|---|---|---|---|---|---|
| GNLY | 102191341 | granulysin | 32.21 | 149.78 | −2.21 |
| ASAP3 | 102182646 | ArfGAP with SH3 domain ankyrin repeat and PH domain 3 | 15.62 | 70.26 | −2.18 |
| LOC108633178 | 108633178 | granzyme B-like | 6.6 | 50.4 | −2.98 |
| TBKBP1 | 102172659 | TBK1 binding protein | 74.03 | 499.27 | −2.76 |
| SLC17A7 | 102169042 | solute carrier family 17 member 7 | 3.1 | 53.98 | −4.10 |
| FAM198B | 102191727 | family with sequence similarity 198 member B | 768.85 | 311.61 | 1.30 |
| AOAH | 102189546 | acyloxyacyl hydrolase | 268.21 | 1014.3 | −1.92 |

TABLE 4A

Use of host genes, for example, as measured by quantitative PCR, to differentiate between naïve, infected, and vaccinated animals

| Status of the Animal | Relative expression of FAM198B | Relative expression of AOAH |
|---|---|---|
| Naïve | 1 | 1 |
| Infected | 6.89 | 1.10 |
| Vaccinated with LAV vaccine | 3.49 | 10.47 |

TABLE 4B

Summary of biomarkers for use in differentiation of infected and vaccinated animals.

| | FAM198B | AOAH | MEI1 | IL-22 | CDCP1 |
|---|---|---|---|---|---|
| Infected with MAP vs. Naïve animas | 6.89 | 1.1 | −1.58 | −3.84 | −1.05 |
| Vaccinated with LAV vaccine vs. Naïve Animals | 3.49 | 10.47 | −3.17 | −1.29 | 1.64 |

Applicants envision that the biomarker may include genes or the polynucleotides containing less than an entire gene sequence of the above genes. The biomarker of genes or the polynucleotides may be either single- or double-stranded nucleic acids. A polynucleotide may be RNA, DNA, cDNA, genomic DNA, chemically synthesized RNA or DNA or combinations thereof. The polynucleotides can be purified free of other components, such as proteins, lipids and other polynucleotides. For example, the polynucleotide may be 50%, 75%, 90%, 95%, 96%, 97%, 98%, 99%, or 100% purified. The purified polynucleotides may comprise additional heterologous nucleotides. The purified polynucleotides of the invention can also comprise other nucleotide sequences, such as sequences coding for linkers, primer, signal sequences, TMR stop transfer sequences, transmembrane domains, or ligands.

The gene or the polynucleotides of the invention may also comprise fragments that encode immunogenic polypeptides. Polynucleotides of the invention may encode full-length polypeptides, polypeptide fragments, and variant or fusion polypeptides. Polynucleotides of the invention may comprise coding sequences for naturally occurring polypeptides or may encode altered sequences that do not occur in nature. If desired, polynucleotides may be cloned into an expression vector comprising expression control elements, including for example, origins of replication, promoters, enhancers, or other regulatory elements that drive expression of the polynucleotides of the invention in host cells.

Detection of Biomarkers or Markers

The present biomarkers or markers may be detected by any suitable method. In one embodiment, the testing is via ELISA assay for antibodies formed against the biomarkers or markers.

The biomarker or marker in the present invention may be directly detected, e.g., by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag.

For example, detecting and/or quantifying may be performed by one or more method(s) selected from the group consisting of: SELDI (-TOF), MALDI (-TOF), a 1-D gel-based analysis, a 2-D gel-based analysis, Mass spectrometry (MS), reverse phase (RP) LC, size permeation (gel filtration), ion exchange, affinity, HPLC, UPLC and other LC or LC MS-based techniques. Appropriate LC MS techniques may include ICAT® (Applied Biosystems, CA, USA), or iTRAQ® (Applied Biosystems, CA, USA). Liquid chromatography (e.g., high pressure liquid chromatography (HPLC) or low pressure liquid chromatography (LPLC)), thin-layer chromatography, NMR (nuclear magnetic resonance) spectroscopy may also be used. Methods of diagnosing and/or monitoring according to the invention may comprise analyzing a plasma, serum or whole blood sample by a sandwich immunoassay to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the biomarkers or markers may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g., using gold, silver, or latex particles, magnetic particles, or Q-dots). Immunological methods may be performed, for example, in microtiter plate or strip format.

The gene or the polynucleotides of the invention may be detected by, for example, a probe or primer or a PCR primer. The gene or the polynucleotides of the invention may be the basis for designing a complimentary probe or primer, to detect the presence and/or quantity of biomarker in a subject, such as a biological sample. Probes are molecules capable of interacting with a target nucleic acid, typically in a sequence specific manner, for example, through hybridization. Primers are a subset of probes that can support specific enzymatic manipulation and that can hybridize with a target nucleic acid such that the enzymatic manipulation occurs. A primer may be made from any combination of nucleotides or nucleotide derivatives or analogs available in the art that do not interfere with the enzymatic manipulation. "Specific" means that a gene sequence recognizes or matches another gene of the invention with greater affinity than to other non-specific molecules. Preferably, "specifically binds" or "specific to" also means a gene sequence recognizes and matches a gene sequence comprised in a biomarker described herein, with greater affinity than to other non-specific molecules.

The hybridization of nucleic acids is well understood in the art. Typically a primer may be made from any combination of nucleotides or nucleotide derivatives or analogs available in the art. The ability of such primers to specifically hybridize to polynucleotide sequences of the recited biomarkers will enable them to be of use in detecting the presence of complementary sequences in a given subject. The primers of the invention may hybridize to complementary sequences in a subject such as a biological sample, including, without limitation, saliva, sputum, blood, plasma, serum, urine, feces, cerebrospinal fluid, amniotic fluid, wound exudate, or tissue of the subject. Polynucleotides from the sample can be, for example, subjected to gel electrophoresis or other size separation techniques or can be immobilized without size separation.

The probes or the primers may also be labeled for the detection. Suitable labels, and methods for labeling primers are known in the art. For example, the label may include, without limitation, radioactive labels, biotin labels, fluorescent labels, chemiluminescent labels, bioluminescent labels, metal chelator labels and enzyme labels. The polynucleotides from the sample are contacted with the probes or primers under hybridization conditions of suitable stringencies. Preferably, the primer is fluorescently labeled. Also, the detection of the presence or quality of the gene sequence of interest can be accomplished by any method known in the art. For instance, the detection can be made by a DNA amplification reaction. In some embodiments, "amplification" of DNA denotes the use of polymerase chain reaction (PCR) to increase the concentration of a particular DNA sequence within a mixtures of DNA sequences.

In some embodiments, quantitative polymerase chain reaction (qPCR) or real-time quantitative polymerase chain reaction (RT-qPCR) is used to measure expression levels of nucleotide biomarkers. These methods detect and quantify the products generated during each cycle of the PCR process which are directly proportionate to the amount of the messenger RNA, DNA, or cDNA prior to the start of the PCR process. Some qPCR and RT-qPCR methods may use non-specific fluorescent dyes that intercalate with any double stranded DNA or sequence specific DNA probes with fluorescently labeled oligonucleotides to permit detection only after hybridization of the probe with the complementary sequence. Suitable RT-qPCR and qPCR methods, probes and dyes are known in the art.

In another embodiment, the amplification of DNA may be done by the loop-mediated isothermal amplification (LAMP). Similar to PCR, LAMP utilizes a polymerization-based reaction to amplify DNA from examined samples, but the enzyme for LAMP, Bst DNA polymerase large fragment, possesses a DNA strand displacement activity. This makes the DNA extension step possible without having to fully denature DNA templates. Moreover, the primers are designed in a way that a hairpin loop structure is formed in the first cycle of amplification, and the following products are further amplified in an auto-cycling manner. Therefore, in about an hour, the repeated reactions can amplify by $\sim 10^9$ copies of DNA molecules and can be done at a constant temperature in a single heat block, instead of at various cycles of temperature in a relatively expensive thermal cycler. The detection of LAMP has been described in PCT patent application publication WO20141640055A1, which is incorporated herein in its entirety.

In one embodiment, the detection of the presence of the gene or the specific binding between the gene in *mycobacterium* mutant and a gene that is not a component of a subject's immune response to a particular vaccine may indicate a natural or experimental *mycobacterium* infection. For example, the absence of such binding or presence may indicate the absence of *mycobacterium* infection. Or, a second, separate gene, such as a mutated *mycobacterium* gene that is specific to a component of a mammal's immune response to a particular *mycobacterium* vaccine, may be used to detect corresponding antibodies produced in response to vaccination. Thus, if an antibody specific to a gene in *mycobacterium* vaccine is detected, then the mammal has been vaccinated and/or infected. The detection of neither genes indicates no infection and no vaccination. As such, various combinations can lead to a determination of the vaccination and/or infection status of the mammal.

Kits of the Present Invention

In another aspect, the present invention discloses a diagnostic kit suitable for carrying out the diagnostic method of the first aspect of the invention. In one embodiment, the kit may be a "one-day" kit, meaning that it is capable of providing the diagnostic result within one day of sample collection. In another embodiment, the kit may be able to provide a diagnostic result within 12, 10, 8, 6, 4, 2, 1 or 0.5 hours of sample collection.

In one embodiment, the diagnostic kit may be used for early detection of mycobacterial infection in a mammal. The diagnostic kit may also be used to differentiate a vaccinated mammal from an infected mammal.

In one embodiment, the diagnostic kit may be portable. The portable diagnostic kit may specifically suitable for field testing. Applicants envision that the present diagnostic kit may be used in a farm field such as a milk farm, where farmers/veterinarians may collect samples and run the assay on the field (point of care assay) to identify early stages of Johne's disease infection and to differentiate infected from vaccinated mammals.

The kit may include a substrate. In one embodiment, the substrate may be coated with biomolecules such as antibodies, which are specifically binding to the specific biomarkers as discussed above. The biomolecules may further possess a detectable label, such as a luminescent, fluorescent or radioactive label, and/or an affinity tag.

In one embodiment of the present invention, the substrate may be used as a sample holder. Exemplary substrates may include microtiter strips or plates. In one specific embodiment, a sample such as a diluted serum may be pipetted into the wells of the microtiter plate or strip. A binding between the biomarkers in the serum and the biomolecules takes place. The presence or absence of the specific biomarkers or a combination of biomarkers as discussed above may indicate the infection status of the mammal.

The kit may further include a means of detection. The means of detection may include any detection method as discussed above. In one embodiment, the means of detection may be a spectroscopic technique, such as UV-Vis or MS. In one specific embodiment, the means of detection may be ELISA.

In one embodiment, the kit may include standard data for specific biomarker or a combination of biomarkers as discussed. One may compare the test result of a mammalian sample with the standard data for specific biomarker or a combination of biomarkers to determine the infection status of the mammal. For example, specific biomarkers or a combination of biomarkers may be visualized by a simple means of detection such as different colors. The detection result (e.g., showing one specific color) of a mammalian sample may be compared with the standard data (e.g., different colors for different biomarkers) to determine the infection status of the mammals.

In one embodiment, the kit may also be in the form of reagents (e.g. protein extract) that can be inoculated into animals to estimate the level of cell-mediated immunity (e.g. single intradermal comparative skin test, SICST). The reagents may include any of the biomarkers as discussed above. In one embodiment, the reagents may also include any genetically engineered vaccines. Suitable genetically engineered vaccines may include those Applicants previously proposed in PCT patent application publication WO20141640055A1, which is incorporated herein in its entirety.

The diagnostic kit may also include one or more of the following: instructions for use (detailing the method of the first aspect of the invention); sample collection apparatus (such as a needle and syringe); a chart for interpretation of the results; an electronic readout system; software providing a database for accurate data management.

The present invention has been described in terms of one or more preferred embodiments, and it should be appreciated that many equivalents, alternatives, variations, and modifications, aside from those expressly stated, are possible and within the scope of the invention.

EXAMPLES

Example 1—Proteomic Analysis of *M. avium* Subsp. *Paratuberculosis* Vaccine Candidates Johne's disease (JD) is a worldwide health problem for dairy herds that carries a heavy economic burden for producing safe food. Infected cattle suffer from chronic diarrhea, weight loss, low milk yield and low, but persistent mortality (1). For the dairy industry alone, the economic losses caused by JD are estimated to range between $200-$500 million annually, in the USA alone (2, 3). Identifying protective vaccine candidates against JD could be the cornerstone of controlling this widespread infection. In our group, we deciphered genomic information available for *M. ap* to identify key gene regulators that could control the expression of large number of genes. Throughout the genome of *M. ap* there are 19 sigma factors that act as global gene regulators that could contribute to the ability of *M. ap* to grow in many environments (4). Through previous funding from USDA, we examined several *M. ap* sigma (σ) factors that were important for growth in murine macrophages. Using transcriptional profiling, we compared mid-log phase *M. ap* to *M. ap* that had infected IFN-γ activated macrophages for 2 and 24 hours. Of the 19 sigma factors monitored, 6 sigma factor transcripts were up-regulated and one sigma factor transcript was down-regulated during the 24 hour time frame. Of the up-regulated transcripts, the sigL transcript was the only transcript up-regulated 2 hours after infection while sigH was up-regulated at 24 hrs (5). SigL is implicated in cell membrane protein biosynthesis as well as virulence in *M. tuberculosis* (6) while SigH was shown to be involved in combating the host intracellular responses such as oxidative stress (7).

To assess the role of sigL and sigH in *M. ap* virulence, we replaced the target sigma factors gene coding regions with a hygromycin-resistant gene cassette in *M. ap* K-10 using a specialized transduction protocol that was adapted for *M. ap*. Both genes were shown to be necessary for *M. ap* virulence in different stages of murine infection as detailed before (5, 8). Interestingly, the same mutants were shown to provide protective immunity against challenge with the virulent strain of *M. ap* when they were used as vaccine candidates in mice. To better analyze proteins expressed in each mutant, we grow cultures of *M. ap* ΔIsigL, *M. ap* ΔsigH mutants and the wild type parent strain, *M. ap* K10 to mid-log phase. All cultures were washed twice in PBS, resuspended in buffer cocktail with endonuclease before proteomic analysis using nano-Liquid Chromatography-Mass Spectroscopy-MS (nano-LC MS/MS) at the University of Wisconsin Biotechnology Center. From 3 biological replicates, a total of ~900 proteins were identified in this analysis comparing sigL and sigH mutant to *M. ap* K10 proteome.

Diagnostic Markers for JD-Vaccinated Animals.

A major problem in employing mass vaccination program for the control of JD in dairy herds is the inability to differentiate between infected and vaccinated animals with the current vaccine (DIVA principal). In addition, vaccinated animals could not be differentiated from positive reaction to the infection with *M. bovis*, a significant health problem for domesticated and wildlife animals. However, the DIVA principal and ability to distinguish between *M. bovis* and JD vaccinated animals could be achieved in genetically engineered vaccines (such as live attenuated vaccines based on sigL and sigH mutant) using a novel approach designed by the Applicant. In this approach, a simple blood test targeting proteins or sequences present in *M. ap* wild type strain and with lower expression level in the vaccine strain or even not encoded in the *M. bovis* genome would be developed. The target proteins include the following list of genes that could be used for the sigL-based vaccines.

TABLE 5

*M. ap* proteins that are significantly over-expressed in the wild type strain and not in the sigL-vaccine and could be used for sigL-DIVA testing.

| Number | Accession Number | Fold Change (K10/sigH) | Name/Function |
|---|---|---|---|
| 1 | Q73SF4 | 1.75 | hypothetical protein |
| 2 | Q73Y73 | 2.66 | aldehyde dehydrogenase (NAD+) |
| 3 | Q73ZE6 | 2.13 | nucleotide-sugar epimerase EpiA |
| 4 | Q73SL7 | 2.69 | hypothetical protein Mb0574c |
| 5 | Q73VK6 | 1.14 | oxidoreductase |
| 6 | Q73XZ0 | 1.88 | antigen CFP2 |
| 7 | Q740D1 | 4.71 | peptide synthetase Nrp |
| 8 | Q73UE0 | 1.99 | cutinase |

TABLE 6

*M. ap* proteins that are significantly over-expressed in the wild type strain and not in the sigH-vaccine and could be used for sigH-DIVA testing.

| Number | Accession Number | Fold Change (WT/sigH) | Name/Function |
|---|---|---|---|
| 1 | Q73VL6 | 3.05 | diguanylate cyclase (GGDEF) domain-containing protein |
| 2 | Q73YW9 | 1.64 | PE family protein, partial |
| 3 | Q741L4 | 1.88 | hypothetical protein |
| 4 | Q744E5 | 2.67 | ABC transporter ATPase |
| 5 | Q73YP5 | 2.47 | Pup--protein ligase |
| 6 | Q73WE5 | 1.78 | arginine decarboxylase |
| 7 | Q73U21 | 1.88 | PE family protein PE17 |
| 8 | Q73UH9 | 2.16 | XRE family transcriptional regulator |
| 9 | Q741M5 | 2.11 | nitroreductase |
| 10 | Q742F4 | 2.72 | metallo-beta-lactamase |
| 11 | Q73SU6 | 2.47 | 3-ketoacyl-ACP reductase |

In addition, another vaccine candidate is based on lipN mutant. In this case, epitopes that are different in the *M. ap* protein compared to those in *M. bovis* will be the target for DIVA diagnostic test.

FIG. 1 shows the alignment plot of amino acids deduced from the protein sequence in LipN of both *M. paratuberculosis* and *M. bovis*. Peptides conserved in *M. paratuberculosis* sequence but absent from *M. bovis* would be the target for developing the DIVA test.

Example 2—Biomarkers for Early Diagnosis and Differentiation of Mycobacterial Infections Johne's disease, caused by *Mycobacterium avium* subspecies *paratuberculosis* (MAP) is a chronic gastroenteritis of ruminants. Although infection often occurs within the first few months of life, clinical signs do not appear until 2-5 years of age. Current diagnostic tests, such as fecal culture and ELISA, have poor sensitivity for detection of the sub-clinical phase of disease. Therefore, biomarkers have been increasingly investigated as a method for sub-clinical detection.

In this project, we set out to develop rapid assays (e.g. PCR or field skin test) for early detection of presence of Johne's disease and for the differentiation of Johne's disease vaccinated vs. infected animals (with MAP or *M. bovis*). To speed up the project outcome, we capitalized on ongoing vaccine study in goats (*Capra hircus*) and collected Peripheral blood mononuclear cells (PBMC's) for transcriptional profiling followed by gene prediction for disease initiation and progression.

The PBMC's have been shown to be a predictor of infection and inflammatory disease. The PBMC transcriptomes of the goats were profiled using RNA-sequencing (RNA-Seq) to evaluate differential gene expression between a subset of samples from either 30 days post-vaccination, 30 days post-infection, or a naive, non-infected control group (3-4 biological replicates per group). Preliminary results on differential gene expression indicated the presence of 88 significantly differentially expressed genes out of 11,009 genes between goats at 30 days post-infection and the naïve, non-infected controls. The 30 days post-vaccination group had 720 out of 10,985 and 746 out of 11,099 significantly differentially expressed genes compared to the naïve, non-infected control group and the 30 days post-infection group, respectively. However, preliminary evaluation of the expressed genes indicated a large number of genes with immunological and inflammatory functions, including IL-18 binding protein, IFN-γ, IL-17A, and IL-22. Because of this inquiry, Table 7 summarizes selected genes/targets suitable to use in the present invention.

TABLE 7

List of DNA markers that are derived from the host transcriptome analysis and can be used for early diagnosis of Johne's disease in ruminants (cattle, goats, sheep and camels).

| Locus in goats | Symbol | Protein | Description | Homolog in Bos taurus (cows) | Homolog description |
|---|---|---|---|---|---|
| Selected list of host (goat and cow) markers that can differentiate infected from naïve animals. | | | | | |
| NW_005125111.1: 0-184 | unplaced genomic scaffold | N/A | N/A | | |
| NW_005101181.1: 1703-1858 | unplaced genomic scaffold | N/A | N/A | | |
| NW_005101181.1: 168292-168418 | LOC102180841 | XP_005701370.1 | PREDICTED: multidrug resistance-associated protein 4-like | XP_005199610 | multidrug resistance-associated protein 4-like isoform X1 |
| NC_022320.1: 39973839-39974080 | Non-coding region | N/A | N/A | | |
| NC_022297.1: 44037534-44043184 | IL-22 | XP_005680263.1 | interleukin 22 | NP_001091849.1 | interleukin 22 |
| NC_022296.1: 81262820-81263390 | Non-coding region | N/A | N/A | | |
| NW_005101844.1: 141791-142987 | ABCC4 | XP_005701761.1 | PREDICTED: multidrug resistance-associated protein 4-like, partial | XP_010820300.1 | PREDICTED: multidrug resistance-associated protein 4 isoform X1 |
| NW_005101711.1: 48628-48757 | LOC102185556 | XP_005701708.1 | PREDICTED: multidrug resistance-associated protein 4-like | XP_003585348.3 | PREDICTED: multidrug resistance-associated protein 4 isoform X1 |
| NW_005132660.1: 0-240 | unplaced genomic scaffold | N/A | N/A | | |
| NW_005109943.1: 2-224 | unplaced genomic scaffold | N/A | N/A | | |
| NW_005149706.1: 0-366 | unplaced genomic scaffold | N/A | N/A | | |

TABLE 7-continued

List of DNA markers that are derived from the host transcriptome analysis and can be used for early diagnosis of Johne's disease in ruminants (cattle, goats, sheep and camels).

| Locus in goats | Symbol | Protein | Description | Homolog in Bos taurus (cows) | Homolog description |
| --- | --- | --- | --- | --- | --- |
| NW_005153011.1: 2-407 | unplaced genomic scaffold | N/A | N/A | | |
| NW_017189548.1: 2899 ... 17746 | LOC108634521 | N/A | ncRNA | N/A | N/A |
| NC_030819.1: complement (13836329 ... 13914672) | LOC108637251 | N/A | N/A | N/A | multidrug resistance-associated protein 4-like |
| NC_030819.1: 13926013 ... 14000960 | LOC108637252 | N/A | N/A | N/A | multidrug resistance-associated protein 4-like |
| NW_017189646.1: complement (5337 ... 40350) | LOC108634594 | N/A | N/A | N/A | multidrug resistance-associated protein 4-like |
| NC_030824.1: complement (30222726 ... 30294233) | FAM198B | N/A | N/A | N/A | family with sequence similarity 198 member B |
| NC_030822.1: 34764774 ... 34772382 | LOC108637671 | N/A | N/A | N/A | tripartite motif-containing protein 5-like |
| NC_030829.1: 54084869 ... 54144689 | CDCP1 | 102187276 | CUB domain containing protein | XP_002697164; XP_612363 | |
| NC_030812.1: 78337529 ... 78655742 | TMTC1 | 102185637 | transmembrane and tetratricopeptide repeat | N/A | |
| NC_030832.1: 38530654 ... 38607511 | BAIAP2L1 | 102173150 | BAI1 associated protein 2 like | XP_003584109; XM_003584061; XP_003587892; XM_003587844 | |
| NC_030812.1: 111693222 ... 111748937 | MEI1 | 102169168 | meiotic double-stranded break formation protein | NP_001295589 | |
| NC_030818.1: 43871666 ... 43923217 | SEPT10 | 102171885 | septin 10 | NP_001039641 | |
| NC_030812.1: 44984285 ... 44988400 | IFNG | 100860815 | interferon gamma | NP_776511 | |
| NC_030830.1: 24511444 ... 24519042 | IL17F | 102171111 | interleukin 17F | NP_001179011 | |
| NC_030814.1: 93891943 ... 93902156 | FCER2 | 102171507 | Fc fragment of IgE receptor II | N/A | |
| NC_030825.1: 26945415 ... 26990225 | ADGRG1 | 102171366 | G protein-coupled receptor G | NP_001077125 | |
| NC_030822.1: complement (35694810 ... 35718058) | APBB1 | 102179305 | amyloid beta precursor protein binding family B member | NP_001068654 | |
| NC_030815.1: 69261357 ... 69324811 | PIWIL2 | 102173845 | piwi like RNA-mediated gene silencing | XP_015320079; XM_015464593; XP_015328077; XM_015472591 | |

Selected list of host (goat and cow) markers that can differentiate live attenuated vaccinated (LAV) from naïve animals.

| Locus in goats | Symbol | Protein | Description | Homolog in Bos taurus (cows) | Homolog description |
| --- | --- | --- | --- | --- | --- |
| NC_022296.1: 32351255-32351413 | Non-coding region | N/A | N/A | | |
| NC_022307.1: 44045143-44403012 | Non-coding region | N/A | N/A | | |
| NC_022295.1: 13176472-13182094 | Non-coding region | N/A | N/A | | |
| NC_022321.1: 6000551-6000875 | Non-coding region | N/A | N/A | | |
| NW_005126018.1: 16-203 | unplaced genomic scaffold | N/A | N/A | | |
| NW_005101711.1: 48628-48757 | LOC102185556 | XP_005701708.1 | PREDICTED: multidrug resistance-associated protein 4-like | XP_003585348.3 | PREDICTED: multidrug resistance-associated protein 4 isoform X1 |
| NW_005101844.1: 141790-142987 | ABCC4 | XP_005701761.1 | PREDICTED: multidrug resistance-associated protein 4-like, partial | XP_010820300.1 | PREDICTED: multidrug resistance-associated protein 4 isoform X1 |
| NW_005101645.1: 16151-23647 | unplaced genomic scaffold | N/A | N/A | | |
| NW_017189548.1: 2899 ... 17746 | LOC108634521 | 108634521 | ncRNA | | |
| NC_030826.1: complement (19203362 ... 19245850) | NOS2 | 100860742 | nitric oxide synthase 2 | NP_001070267 | |
| NC_030819.1: complement (13836329 ... 13914672) | LOC108637251 | 108637251 | multidrug resistance-associated protein 4-like | | |

TABLE 7-continued

List of DNA markers that are derived from the host transcriptome analysis and can be used
for early diagnosis of Johne's disease in ruminants (cattle, goats, sheep and camels).

| Locus in goats | Symbol | Protein | Description | Homolog in Bos taurus (cows) | Homolog description |
|---|---|---|---|---|---|
| NC_030809.1: 13806906 . . . 13817913 | TINAGL1 | 102169636 | tubulointerstitial nephritis antigen like | XP_015315454; XP_015317919; XP_015315453; XM_015459967; XP_015317918; XM_015462432 | |
| NW_017189666.1: complement (10281 . . . 11678) | RETN | 102170965 | resistin | NP_899206 | |
| NC_030809.1: 65236017 . . . 65240282 | C1QL2 | 102176742 | complement C1q like 2 | NP_001192765 | |
| NC_030810.1: 104057279 . . . 104111513 | TDRD10 | 102174259 | tudor domain containing 10 | XP_005197751; XM_005197694; XP_005203865; XM_005203808 | |
| NC_030817.1: 15809952 . . . 15835252 | TGFB3 | 102189962 | transforming growth factor beta 3 | NP_001094653; XP_005212263; XP_005212264 | |
| NC_030814.1: 96350745 . . . 96400437 | ADGRE2 | 102171592 | adhesion G protein-coupled receptor E2 | | |
| NC_030831.1: 49397175 . . . 49422345 | LIPG | 102191574 | lipase G endothelial type | | |
| NC_030826.1: complement (59803404 . . . 59814242) | KCNJ2 | 102168940 | potassium voltage-gated channel subfamily J member 2 | NP_776798 | |
| NC_030817.1: 51022717 . . . 51074079 | AQP9 | 102181396 | aquaporin 9 | XP_015328629; XM_015473143; XP_015328630; XM_015473144 | |
| NC_030820.1: 66719462 . . . 66768979 | BPI | 102185756 | bactericidal/permeability-increasing protein | NP_776320 | |
| NC_030814.1: 63194434 . . . 63197324 | IL9 | 102179848 | interleukin 9 | XP_015319783; XM_015464297; XP_015327708; XM_015472222 | |
| NC_030818.1: 6611732 . . . 6648492 | IL1R2 | 102186601 | interleukin 1 receptor type 2 | NP_001039675; XP_010808117; XP_010808118 | |
| NC_030818.1: 46359268 . . . 46368303 | IL36B | 102182235 | interleukin 36 beta | XP_002691396; XM_002691350; XP_002700827; XM_002700781 | |
| NC_030812.1: complement (64862983 . . . 64943172) | IGF1 | 100860838 | insulin like growth factor | XP_005206547; XP_015326547; XP_015326549 | |
| NW_017190169.1: complement (56783 . . . 70690) | BGN | 102183219 | biglycan | NP_847888; XP_005227715 | |
| NC_030815.1: 69261357 . . . 69324811 | PIWIL2 | 102173845 | piwi like RNA-mediated gene silencing | XP_015320079; XM_015464593; XP_015328077; XM_015472591 | |
| NC_030816.1: 74364855 . . . 74372073 | RAET1E | 108636743 | retinoic acid early transcript | | |
| NC_030810.1: complement (105983749 . . . 105989432) | CRABP2 | 102174348 | cellular retinoic acid binding protein 2 | NP_001008670 | |

Selected list of host (goat and cow) markers that can differentiate
inactivated-vaccine immunized from naïve animals.

| Locus in goats | Symbol | Protein | Description | Homolog in Bos taurus (cows) | Homolog description |
|---|---|---|---|---|---|
| NW_005125111.1: 0-184 | unplaced genomic scaffold | N/A | N/A | | |
| NC_022320.1: 39973839-39974080 | Non-coding region | N/A | N/A | | |
| NC_022303.1: 46207878-46237242 | Non-coding region | N/A | N/A | | |
| NC_022296.1: 81262820-81263390 | Non-coding region | N/A | N/A | | |
| NW_005101711.1: 48628-48757 | LOC102185556 | XP_005701708.1 | PREDICTED: multidrug resistance-associated protein 4-like | XP_003585348.3 | PREDICTED: multidrug resistance-associated protein 4 isoform X1 |

TABLE 7-continued

List of DNA markers that are derived from the host transcriptome analysis and can be used for early diagnosis of Johne's disease in ruminants (cattle, goats, sheep and camels).

| Locus in goats | Symbol | Protein | Description | Homolog in Bos taurus (cows) | Homolog description |
|---|---|---|---|---|---|
| NW_005102056.1: 2049-9786 | LOC102190036 | XP_005701827.1 | PREDICTED: tyrosine-protein phosphatase non-receptor type substrate 1-like, partial | NP_786982.1 | tyrosine-protein phosphatase non-receptor type substrate 1 precursor |
| NC_022309.1: 40520580-40588889 | — | XP_005691363.1 | PREDICTED: protein FAM198B | NP_001077247.1 | protein FAM198B |
| NW_005101931.1: 48185-54192 | LOC102180487 | XP_005701808.1 | PREDICTED: interferon alpha-inducible protein 27-like protein 2-like | NP_001069925.2 | uncharacterized protein LOC617420 |
| NW_005164924.1: 1-636 | unplaced genomic scaffold | N/A | N/A | | |
| Selected list of host (goat and cow) markers that can differentiate LAV-vaccine immunized from infected animals. | | | | | |
| NC_030826.1: 39149778 . . . 39151507 | LOC106503226 | 106503226 | | | |
| NC_030826.1: complement (32435859 . . . 32463764) | PMP22 | 102184371 | peripheral myelin protein 22 | NP_001094626; XP_005220437; XP_010814341 | |
| NC_030822.1: complement (31912716 . . . 31916296) | ART5 | 102169686 | ADP-ribosyl-transferase 5 | | |
| NC_030822.1: complement (31947901 . . . 31951735) | LOC102169116 | 102169116 | ecto-ADP-ribosyl-transferase 5 | | |
| NC_030818.1: complement (48786756 . . . 48789216) | GNLY | 102191341 | granulysin | NP_001068611 | |
| NC_030809.1: complement (6533315 . . . 6583406) | ASAP3 | 102182646 | ArfGAP with SH3 domain ankyrin repeat and PH domain 3 | NP_001076915 | |
| NC_030828.1: complement (69374237 . . . 69377734) | LOC108633178 | 108633178 | granzyme B-like | | |
| NC_030826.1: complement (38379103 . . . 38396803) | TBKBP1 | 102172659 | TBK1 binding protein | XP_001253301; XP_005195770; XP_005220704; XP_010814497; XP_010822429; XP_015314281 | |
| NC_030825.1: complement (56899764 . . . 56911150) | SLC17A7 | 102169042 | solute carrier family 17 member 7 | NP_001091515 | |
| NC_030826.1: 53112179 . . . 53116348 | LOC108638192 | 108638192 | | | |
| NC_030812.1: 44984285 . . . 44988400 | IFNG | 100860815 | interferon gamma | NP_776511 | |

Materials and Methods

Animals—Approximately one week-old kids were purchased from a farm with no previous history of Johne's disease. All study kids, and their dams, tested negative for *M. paratuberculosis* by ELISA for serum antibody (Paracheck®, Biocor Animal Health, Omaha, NE). Additionally, fecal samples collected from the originating farm environment were negative for *M. paratuberculosis* by culture. All kids were housed in a restricted biosafety animal facility (BSL-2). All animal care was handled in accordance to the standards of the University of Wisconsin-Madison Animal Care and Use Committee. The kids were randomly assigned to one of four groups as shown in Table 8. One group of kids (n=6 but only 4 used for transcriptome analysis) were vaccinated with a live-attenuated vaccine (LAV) construct (*M. paratuberculosis* ΔlipN mutant (Wu et al., 2007)) at a dose of 1×10$^9$ CFU/animal. The second groups of kids (n=4) were vaccinated with the USDA-licensed inactivated vaccine (Mycopar®). A third group inoculated with PBS served as the vaccine control. Both vaccines and PBS were given subcutaneously. At 60 days post-vaccination, kids in these three groups were inoculated with *M. paratuberculosis* strain JTC1285 at a dose of 1×10$^8$ CFU administered orally in the milk replacer for three consecutive days. A fourth group (n=4), inoculated with PBS and not challenged with *M. paratuberculosis* served as a naïve control. Goat kids were monitored daily for signs of clinical disease and evaluated monthly for potential weight loss. A detailed report on the outcome of this vaccine/challenge study was previously published (Shippy et al., 2017).

TABLE 8

Experimental Groups

| Group | No. | Vaccine* | Vaccine Dose | Challenge Strain/Dose** |
|---|---|---|---|---|
| Infected | 4 | PBS | 0.5 ml | *M. paratuberculosis* JTC1285/ 1 × 10$^8$ CFU |
| LAV-vaccinated | 4 | *M. ap* ΔlipN | 1 × 10$^9$ CFU | *M. paratuberculosis* JTC1285/ 1× 10$^8$ CFU |

TABLE 8-continued

Experimental Groups

| Group | No. | Vaccine* | Vaccine Dose | Challenge Strain/Dose** |
|---|---|---|---|---|
| Mycopar-vaccinated | 3 | Mycopar ® | 0.5 ml | *M. paratuberculosis* JTC1285/ 1 × 10$^8$ CFU |
| Naïve Control | 4 | PBS | 0.5 ml | None |

*All vaccines were given subcutaneously.
**Challenge dose was given orally in milk replacer for three consecutive days and was performed at 60 days post-vaccination in LAV- and Mycopar- vaccinated groups.

Isolation of blood cells—Blood samples (10 ml) were collected from the jugular vein of goats into EDTA vacutainer tubes pre-vaccination, 1 week, 30 days, 60 days post-vaccination and 1 week post-challenge (for 3 groups), and then monthly for 12 months. Peripheral blood mononuclear cells (PBMC) were isolated using Histopaque®-1077 (Sigma-Aldrich®) with the following modifications. Anti-coagulated blood was diluted with an equal volume of RPMI-1640 medium (Sigma Aldrich®), layered over 10 ml of Histopaque®-1077, and centrifuged at 400×g for 30 minutes at room temperature. Following centrifugation, PBMC's were aspirated from the interface and washed twice with RPMI-1640 medium. Residual red blood cells were lysed with 0.83% $NH_4Cl_2$. The PBMC's were then resuspended in complete culture medium (RPMI-1640 containing 10% fetal bovine serum, 1% L-glutamine, 1% penicillin/streptomycin (final concentration 100 IU/ml), and 1% non-essential amino acids). Cell density was determined by use of 0.4% Trypan blue stain and a hemocytometer.

PBMC stimulation and RNA extraction—PBMC's were plated at a density of 1×10$^6$/well in 96 well plates with either medium alone (non-stimulated) or *M. paratuberculosis* whole cell lysate (WCL). The WCL was prepared by resuspending the centrifuged cell pellet of actively grown *M. paratuberculosis* (O.D.~1.0) in protein lysis buffer (100 mM Tris-Cl, 100 mM NaCl, 5 mM $MgCl_2$, 1 mM PMSF, complete ultra-protease inhibitor cocktail (Roche, Indianapolis, IN; pH 7.5) and bead-beating to homogenize (maximum pulse for 45 sec for a total of 4 pulses; with cooling on on ice for 30 sec between pulses). The supernatant was then transferred to a new 1.5 ml tube and non-soluble material was removed by centrifugation at 10,000×g for 5 min at 4° C. The protein content of the supernatant was measured via the Pierce™ BCA protein assay (Thermo Fisher Scientific), aliquoted and stored at −80° C. until used. Final concentrations of WCL was 10 µg/ml. IL-2 was added to all wells at a concentration of 100 U/ml. Plates were incubated at 37° C. with 5% $CO_2$ for 24 hours. Supernatants were then removed and cell pellets were stored in 100 µl TRIzol® and frozen at −80° C. until used for RNA extraction. RNA was extracted from stimulated PBMC's using TRIzol® and RNeasy® Mini Kit (Qiagen®) according to manufacturer's directions for the remainder of the extraction. TURBO DNA-Free™ DNase Treatment (Ambion®) was used to eliminate residual genomic DNA. RNA quantity and quality was assessed using the RNA Pico Series Chip on the Bioanalyzer 2100 (Agilent). RNA integrity numbers (RINs)>8 were obtained for all total RNA samples purified.

RNA Sequence Analysis—RNA-Sequencing (RNA-Seq) was performed by the University of Wisconsin-Madison Biotechnology Center on RNA extracted from WCL-stimulated PBMC's from goats at 30 days post-vaccination, 30 days post-challenge (PBS vaccinated), or at the same time for the naïve control group (4 goats/biological replicates per group). A total of 1 µg of RNA was used as input for TruSeq® RNA Sample Prep Rev.F (March 2014; Illumina®). Paired-end RNA Sequencing was performed on the Illumina HiSeq 2000 sequencer according to manufacturer's instructions.

Raw RNA-Seq reads were uploaded to CLC Genomics Workbench 8.5 (Qiagen, Redwood City, CA) for processing. Two read files from one RNA sample were paired and trimmed. The ambiguous trim limit was set at 1 and quality trim limit was at 0.05. Reads shorter than 25 nucleotides were excluded. The trimmed sequences were then mapped to the reference genome sequence of *Capra hircus* assembly ARS1 (Bickhart et al., 2017) and read counts against the reference genome annotation tracks, generated with files, available at ncbi.nlm.nih.gov/genomes/Capra_hircus, were compiled and tabulated using the CLC Genomics Workbench NGS tools. The mapping parameters were set as follows: mismatch cost, 2; insertion and deletion cost, 3; length and similarity fraction, 0.8. Unique gene reads from each sample were exported from CLC Genomics Workbench and used for normalization and differential gene expression analysis with an R package, DESeq2 version 1.16.1 (Love et al., 2014). Transcripts that had an average of normalized read count<3 in all three tested groups were excluded from the analysis (N=11,541). Differentially expressed transcripts are defined as transcripts with fold changes≥2.0 or ≤−2.0 (or Loge-transformed fold changes≥1.0 or ≤−1.0), and p-value<0.05 when compared to the naïve control group.

Gene ontology (GO) analysis was performed for the differentially expressed genes with agriGO, an automated tool to identify enriched GO terms, which is specially focused on agricultural species (Du et al., 2010). The gene products are categorized with respect to biological processes, cellular components, and molecular functions. Because the gene ontology in the goat genome is poorly annotated, we chose the *Bos taurus* ENSEMBL genome B2G list (2010 version) as the reference genome. Goat genes (assembly ARS1) with an Entrez gene name were mapped to the counterparts in the bovine genome, resulting in a total gene list of 9,115 GO-annotated genes. Goat DE genes identified in the RNA-Seq analysis were also mapped to the bovine genome and used as query lists against the 9,115-gene reference. FDR was calculated using the Fisher test.

Network analysis was performed using the STRING database (Szklarczyk et al., 2015) with DE transcripts identified in this study. The input DE transcripts were treated as homologues of *Bos taurus* because of availability in the database.

Quantitative RT-PCR—cDNA was synthesized from each RNA sample using SuperScript III Reverse Transcriptase (Invitrogen, Waltham, MA) and oligo(dT)$_{12-18}$ Primer according to manufacturer's instructions. Quantitative PCR (qPCR) assays were performed in triplicates for each cDNA sample. Primers were designed across adjacent exons in order to differentiate products from genomic DNA and cDNA. The GAPDH gene served as an internal control to normalize the data for the ΔΔCt relative quantitation method. The assays were performed on an Applied Biosystems StepOne Plus Real-Time PCR System (Foster City, CA), and the cDNA amplifications were monitored by the measurement of SYBR Green fluorescence at a specific cycle threshold. Each reaction was carried out in a 20 µl volume that contained 10 µl of 2× GoTaq qPCR Master Mix (Promega, Madison, WI), 5.0 µl of ddH2O, 0.5 µl of each primer (10 µm) and 4.0 µl of the template (100-150 ng/ul). The qPCR amplification process began with the temperature at 95° C. for 2 min, followed by 40 cycles of the amplification process (95° C. for 3 s, 60° C. for 30 s). Subsequent to the cycling process, melting curves were generated by inclining the temperature from 60° C. to 95° C. at 0.3° C./s increments. With the exception of the infected group at 1 month post-challenge where two samples were used, cDNA samples from three animals in each group were included in the qPCR analysis. Average ΔΔCt values and standard errors of the mean (SEM) of the three measurements were calculated and transformed to linear fold change.

qRT-PCR primers

| Primer ID | Primer name | Primer sequence | SEQ ID NO: |
|---|---|---|---|
| AMT2341 | SEPT10_F | ggtgagcgccagaggaa | 4 |
| AMT2342 | SEPT10_R | cagcttctcctcttggtggac | 5 |
| AMT2343 | IL18BP_F | aactggatcccagacccc | 6 |
| AMT2344 | IL18BP_R | gtagctgctgggagcgc | 7 |
| AMT2351 | IL17A_F | ggaacacgaactccagaaggc | 8 |
| AMT2352 | IL17A_R | acagagttcatgtgatggtccac | 9 |
| AMT2353 | CRABP2_F | accaccgtgcgtaccac | 10 |
| AMT2354 | CRABP2_R | ggaggtcttgggaccctctc | 11 |
| AMT2355 | IL36_F | cgttaatagcagttccttctagcaac | 12 |
| AMT2356 | IL36_R | ggatagccctggatttctgtgc | 13 |
| AMT2361 | RETN_F | tgaggcagtaaggaacattggc | 14 |
| AMT2362 | RETN_R | agtccatgcctgcgcac | 15 |
| AMT2363 | IFNG_F | gcagctctgagaaactggagg | 16 |
| AMT2364 | IFNG_R | tccggcctcgaaagagattct | 17 |
| AMT2365 | GAPDH_F | ggcgtgaaccacgagaagtataa | 18 |
| AMT2366 | GAPDH_R | ggcagtgatggcgtggac | 19 |
| AMT 2899 | ABCC4_F | cttggatcgccatacccctc | 20 |
| AMT 2900 | ABCC4_R | gggctccgggttgtagattc | 21 |
| AMT 2914 | IL 17F_F | gaggaccacattgtgagggt | 22 |
| AMT 2915 | IL 17F_R | cgggtgatgttgtaatcccag | 23 |
| AMT 2918 | TINAGL1_F | cgacgaggggttgtgtctg | 24 |
| AMT 2919 | TINAGL1_R | acatagctattggggcagcg | 25 |
| AMT 2971 | FAM198B_F | tcatccaagatggccgcc | 26 |
| AMT 2972 | FAM198B_R | gccagcacttctgtttcagc | 27 |
| AMT 2973 | AOAH_F | gaaatcacggaggagtggca | 28 |
| AMT 2974 | AOAH_R | aacagctgtgaaaccacctca | 29 |
| AMT 2988 | IL 22_F | cagggaatcaatcaggtgacga | 30 |
| AMT 2989 | IL 22_R | atgggggtggaattcatcgg | 31 |
| AMT 2992 | MEI1_F | cagtgaagtgctcgtctggt | 32 |
| AMT 2993 | MEI1_R | cgactcaatcccatacaccgt | 33 |
| AMT 2994 | CDCP1_F | aagccaagcttccgctatca | 34 |
| AMT 2995 | CDCP1_R | cgatgacagtcaggtccgtg | 35 |

Results

Transcriptome analysis of goat groups. The transcriptome analysis of goats infected with *M. paratuberculosis* and/or vaccinated LAV vaccine strain *M. ap* ΔlipN is a proportion of a larger study that examined the performance of this vaccine published earlier (Shippy et al., 2017). The transcriptome analysis is the focus of this report. The summary statistics of the RNA-Seq data for each replicate are shown in Table 9. Mean values of 58.88 million raw reads were generated per library (each RNA sample). Following trimming of reads based on read length, quality score and adapter sequences, an average of 20.04 million paired reads remained. Alignment of the trimmed RNA-Seq reads to the *Capra hircus* reference genome yielded mean values per library of 18.71 million paired reads (93.32%) mapped to unique locations.

TABLE 9

Summary statistics for Illumina RNA sequencing data

| Group/Replicate Number* | Total Number of Reads | Number of Read Pairs Being Trimmed | Total Paired Reads After mapping | % Total Paired Reads After Trimming | Uniquely mapped reads | % Uniquely mapped reads |
|---|---|---|---|---|---|---|
| Infected 1 | 73,105,634 | 22,810,292 | 25,147,671 | 68.8 | 23,533,313 | 93.58 |
| Infected 2 | 72,155,108 | 23,491,132 | 24,331,988 | 67.44 | 22,701,378 | 93.30 |
| Infected 3 | 68,005,382 | 21,295,316 | 23,355,033 | 68.69 | 21,941,420 | 93.95 |
| Infected 4 | 48,108,726 | 15,062,194 | 16,523,266 | 68.69 | 15,433,817 | 93.41 |
| LAV-vaccinated 1 | 73,973,058 | 24,360,882 | 24,806,088 | 67.07 | 23,253,486 | 93.74 |
| LAV-vaccinated 2 | 63,076,126 | 20,765,850 | 21,155,138 | 67.08 | 19,668,167 | 92.97 |
| LAV-vaccinated 3 | 34,967,370 | 11,169,558 | 11,898,906 | 68.06 | 11,062,093 | 92.97 |
| LAV-vaccinated 4 | 66,996,260 | 21,387,972 | 22,804,144 | 68.08 | 21,282,727 | 93.33 |
| Mycopar-vaccinated 1 | 60,074,726 | 20,141,682 | 19,966,522 | 66.47 | 18,707,059 | 93.69 |

TABLE 9-continued

Summary statistics for Illumina RNA sequencing data

| Group/Replicate Number* | Total Number of Reads | Number of Read Pairs Being Trimmed | Total Paired Reads After mapping | % Total Paired Reads After Trimming | Uniquely mapped reads | % Uniquely mapped reads |
|---|---|---|---|---|---|---|
| Mycopar-vaccinated 2 | 70,284,036 | 23,645,792 | 23,319,122 | 66.36 | 21,978,596 | 94.25 |
| Mycopar-vaccinated 3 | 64,746,832 | 21,633,920 | 21,556,456 | 66.59 | 20,141,993 | 93.44 |
| Naïve 1 | 73,575,076 | 22,859,182 | 25,357,947 | 68.93 | 23,681,558 | 93.39 |
| Naïve 2 | 50,851,250 | 16,107,620 | 17,371,815 | 68.32 | 16,180,977 | 93.14 |
| Naïve 3 | 46,913,012 | 15,083,746 | 15,914,633 | 67.85 | 14,815,443 | 93.09 |
| Naïve 4 | 34,829,124 | 11,209,870 | 11,809,627 | 67.81 | 10,972,712 | 92.91 |

*Time when blood samples were taken: Infected: 30 days post-infection; LAV-vaccinated: 30 days post-LAV vaccination; Mycopar-vaccinated: 30 days post-Mycopar ® vaccination; Naïve:: 30 days post-PBS vaccination.

Figure 3A:
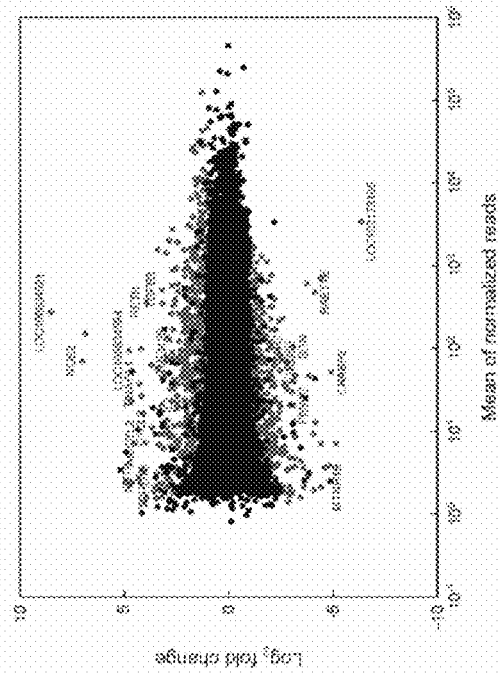
FIGS. 3A-3C show RNA sequencing analysis of different goat groups following infection or vaccination with LAV or Mycopar vaccines. MAplots of (A) the infected group compared to the naïve group, (B) the LAV-vaccinated group compared to the naïve group and (C) the Mycopar-vaccinated group compared to the naïve group are shown. Red dots represent differentially expressed transcripts (fold change>2.0 or <−2.0, p<0.05).
Figure 3B:
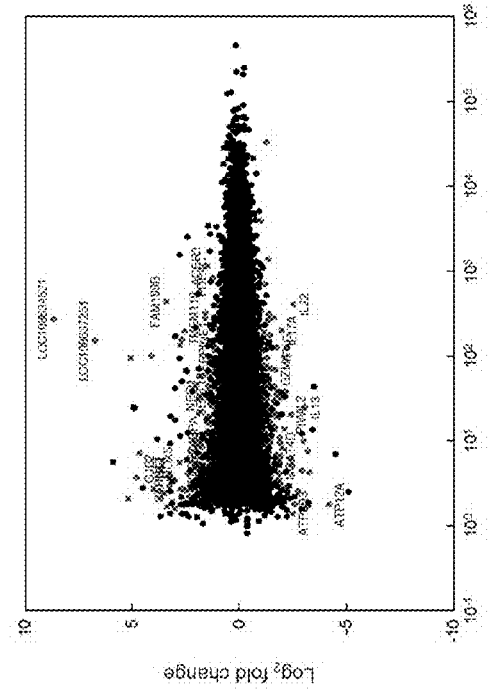
Figure 3C:
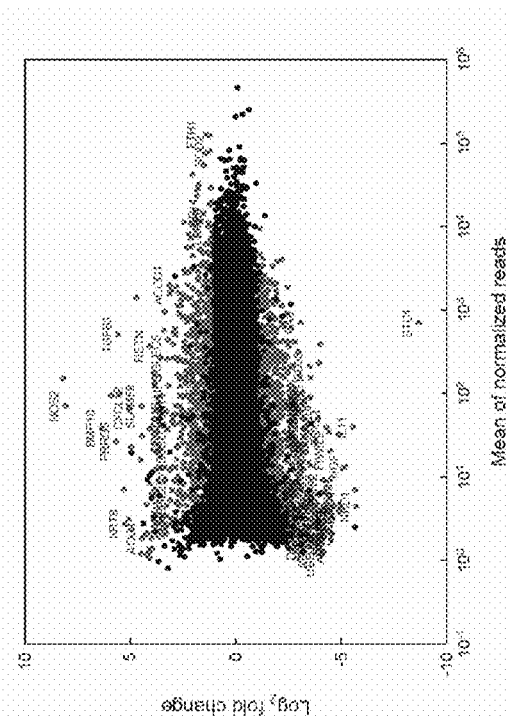

Changes in the goat transcriptomes related to infection or vaccination—Transcriptomes of different animal groups were analyzed to identify differentially expressed (DE) genes with significant change using ap-value threshold of >0.05 and >2-fold change. A summary of comparative numbers of differentially expressed genes is presented in Table 10. MA-plots in FIGS. 3A-3C depict the distributions of the DE transcripts PI and post-vaccination groups compared to naïve control group. Generally, the infected goat group had 226 significantly DE transcripts out of 17,380 (total goat transcripts identified by RNA-Seq) at 30 days PI in comparison to the naïve, non-infected controls. Of the 226 significantly DE transcripts, 113 were up-regulated in the PI group, while the other 113 were down-regulated. A total of 106 out of the 226 DE transcripts had more than a 2.8 fold change (or 1.5 loge fold change) with a selected group of known function listed in Table 11. On the other hand, the LAV-vaccinated goat group had 1018 significantly DE transcripts out of 17,380 compared to the naïve, non-infected control group. A total of 628 and 390 transcripts were up- and down-regulated, respectively. A total of 517 out of the 1018 had >2.8 fold change with a selected group of known function listed in Table 11. Additionally, when the transcripts of both LAV-vaccinated and infected groups were compared, at total of 1133 transcripts were significantly DE out of 17,380 (Table 10). Of these transcripts, 629 and 504 transcripts were up- and down-regulated, respectively. A total of 575 out of the 1133 DE transcripts were greater than a 2.8 fold change. Interestingly, the immunization with the inactivated, oil-based vaccine (Mycopar) triggered significant changes in a large number of goat genes (N=1714) including key genes involved in immune responses (Table 10).

TABLE 10

Differentially Expressed (DE) Genes for each comparison group

| Comparison | Total analyzed Genes | DE Genes* |
|---|---|---|
| Infected vs Naïve | 17,380 | 226 |
| LAV-vaccinated vs Naïve | | 1018 |
| Mycopar-vaccinated vs Naïve | | 1714 |
| LAV-vaccinated vs Infected | | 1133 |

*DE genes were identified as those with a p value threshold of ≤ 0.05

TABLE 11

Selected differentially up- or down-regulated genes by fold change, between 30 days post-infection and naïve groups

| Gene symbol | Gene ID | Fold change | P value | Description |
|---|---|---|---|---|
| FAM198B | 102191727 | 10.70 | 0.0016 | family with sequence similarity 198 member B |
| CDCP1 | 102187276 | 4.06 | 0.0143 | CUB domain containing protein 1 |
| TMTC1 | 102185637 | 3.63 | 0.0217 | transmembrane and tetratricopeptide repeat containing 1 |
| BAIAP2L1 | 102173150 | 3.61 | 0.0196 | BAI1 associated protein 2 like 1 |
| MEI1 | 102169168 | 2.99 | 0.0155 | meiotic double-stranded break formation protein 1 |
| SEPT10 | 102171885 | 2.41 | 0.0239 | septin 10 |
| IFNG | 100860815 | −3.36 | 0.0047 | interferon, gamma |
| IL17F | 102171111 | −2.33 | 0.0098 | interleukin 17F |
| FCER2 | 102171507 | −2.57 | 0.0001 | Fc fragment of IgE receptor II |
| ADGRG1 | 102171366 | −3.43 | 0.0037 | adhesion G protein-coupled receptor G1 |
| APBB1 | 102179305 | −4.47 | 0.0002 | amyloid beta precursor protein binding family B member 1 |
| PIWIL2 | 102173845 | −5.31 | 0.0400 | piwi like RNA-mediated gene silencing 2 |

TABLE 12

Selected differentially up- or down-regulated genes by fold change, between 30 days post-LAV-vaccination and naïve groups

| Gene symbol | Gene ID | Fold change | p-value | Description |
|---|---|---|---|---|
| NOS2 | 100860742 | 130.42 | 2.3E−09 | nitric oxide synthase 2 |
| TINAGL1 | 102169636 | 19.31 | 1.2E−05 | tubulointerstitial nephritis antigen like |
| RETN | 102176742 | 12.91 | 4.4E−13 | resistin |
| C1QL2 | 102176742 | 12.89 | 0.002 | complement C1q like 2 |
| TDRD10 | 102174259 | 11.54 | 0.019 | tudor domain containing 10 |
| TGFB3 | 102189962 | 9.13 | 0.0020 | transforming growth factor beta 3 |
| ADGRE2 | 102171592 | 5.90 | 0.0135 | adhesion G protein-coupled receptor E2 |
| LIPG | 102191574 | 5.28 | 0.0001 | lipase G, endothelial type |
| KCNJ2 | 102168940 | 4.82 | 0.0003 | potassium voltage-gated channel subfamily J member 2 |
| AQP9 | 102181396 | 4.72 | 0.0007 | aquaporin 9 |
| BPI | 102185756 | 3.61 | 0.0140 | bactericidal/permeability-increasing, protein |
| IL9 | 102179848 | −2.91 | 0.0083 | interleukin 9 |
| IL1R2 | 102186601 | −3.63 | 0.0055 | interleukin 1 receptor type 2 |
| IL36B | 102182235 | −5.46 | 0.0013 | interleukin 36 beta |
| IGF1 | 100860838 | −5.46 | 0.0463 | insulin, like, growth, factor, 1 |
| BGN | 102183219 | −8.57 | 0.0045 | biglycan |
| PIWIL2 | 102173845 | −8.57 | 0.009 | piwi like RNA-mediated gene silencing 2 |
| RAET1E | 108636743 | −17.27 | 0.0008 | retinoic acid early transcript 1E |
| CRABP2 | 102174348 | −30.12 | 2.0E−20 | cellular retinoic acid binding protein 2 |

TABLE 13

Selected differentially up- or down-regulated genes by fold change, between 30 days post-Mycopar ®-vaccination and naïve groups

| Gene symbol | Gene ID | Fold change | p-value | Description |
|---|---|---|---|---|
| NOS2 | 100860742 | 269.200 | 3.7E−11 | nitric oxide synthase 2 |
| BMP10 | 102185577 | 82.746 | 0.0003 | bone morphogenetic protein 10 |
| TDRD10 | 102174259 | 18.438 | 0.0061 | tudor domain containing 10 |
| RETN | 102170965 | 16.901 | 4.2E−12 | resistin |
| AMOTL2 | 102169708 | 14.389 | 0.0065 | angiomotin like 2 |
| KLRG2 | 102177407 | 12.733 | 2.9E−10 | killer cell lectin like receptor G2 |
| IL21 | 100861248 | 8.124 | 4.6E−05 | interleukin 21 |
| C2 | 102176085 | 7.95 | 2.4E−7 | complement C2 |
| C3 | 100860826 | 6.495 | 0.0002 | complement C3 |
| MCEMP1 | 102172348 | 6.436 | 7.4E−08 | mast cell expressed membrane protein 1 |
| IL34 | 102173115 | 5.434 | 0.0084 | interleukin 34 |
| IL12A | 100861293 | 3.907 | 0.0035 | interleukin 12A |
| TLR4 | 100860955 | 3.423 | 3.8E−07 | toll like receptor 4 |
| TNF | 100861232 | 3.399 | 0.0003 | tumor necrosis factor |
| IL18 | 100861190 | −4.441 | 3.6E−06 | interleukin 18 |
| IL9 | 102179848 | −4.802 | 0.0012 | interleukin 9 |
| IL9R | 102191479 | −4.961 | 9.4E−08 | interleukin 9 receptor |
| IL5 | 102188034 | −4.964 | 0.0396 | interleukin 5 |
| IL36B | 102182235 | −9.557 | 0.0001 | interleukin 36 beta |
| IL13 | 102187477 | −9.675 | 3.4E−07 | interleukin 13 |
| PIWIL2 | 102173845 | −22.152 | 0.0009 | piwi like RNA-mediated gene silencing 2 |
| IL11 | 102184367 | −46.823 | 1.6E−07 | interleukin 11 |

Several genes involved in immune responses were significantly regulated in all goat groups. For example, leukemia inhibitory factor (LIF), interferon-gamma (IFN-γ), and interleukin 22 (IL-22), were found to be DE genes in the infected group when compared to both the control and the LAV-vaccinated groups. More gene lists are provided in the Tables included in Appendices A-G. In the infected group, LIF was down-regulated by −2.51 fold change when compared to the control group and by 3.84 fold when compared to the vaccinated group. IL-22, a Th17-related cytokine, was also down-regulated by a −5.78 fold in the infected group vs the control group and by −33.82 fold when compared to the LAV-vaccinated group. Interestingly, NOS2 gene involved in controlling infection of a closely related mycobacteria, *M. tuberculosis* (Kutsch et al., 1999; Velez et al., 2009), was significantly induced (>100 fold) in both vaccine groups, suggesting an important role of this gene in adaptive immune responses following immunization with LAV (Table 12) or inactivated (Table 13) vaccine. A group of genes with unique diphasic regulatory responses in both LAV and infected goats included immune response genes (e.g. IFN-γ, Granulysin) as well as basic cell metabolic process (e.g. ART5). This list of genes (Table 14) could expand gene categories utilized as targets for developing a sensitive assay to differentiate infected from vaccinated animals (DIVA).

TABLE 14

Common differentially expressed genes regulated in opposite direction between 30 days post-infection and 30 days post-LAV-vaccinated groups, each compared to the naïve group

| Gene symbol | Gene ID | Fold change in Infected group | Fold change in Vaccinated group | Description |
|---|---|---|---|---|
| LOC106503226 | 106503226 | 2.62 | −2.53 | non-coding RNA |
| PMP22 | 102184371 | 2.11 | −3.46 | peripheral myelin protein 22 |
| ART5 | 102169686 | −2.01 | 3.05 | ADP-ribosyltransferase 5 |
| LOC102169116 | 102169116 | −2.03 | 2.27 | ecto-ADP-ribosyltransferase 5 |
| GNLY | 102191341 | −2.13 | 2.19 | granulysin |
| ASAP3 | 102182646 | −2.16 | 2.10 | ArfGAP with SH3 domain ankyrin repeat and PH domain 3 |
| LOC108633178 | 108633178 | −2.68 | 2.95 | granzyme B-like |
| TBKBP1 | 102172659 | −3.03 | 2.23 | TBK1 binding protein transcript |
| SLC17A7 | 102169042 | −3.12 | 5.50 | solute carrier family 17 member 7 |
| LOC108638192 | 108638192 | −3.27 | 5.28 | non-coding RNA |
| IFNG | 100860815 | −3.36 | 3.89 | interferon gamma |

Figures 4A, 4B, 4C:
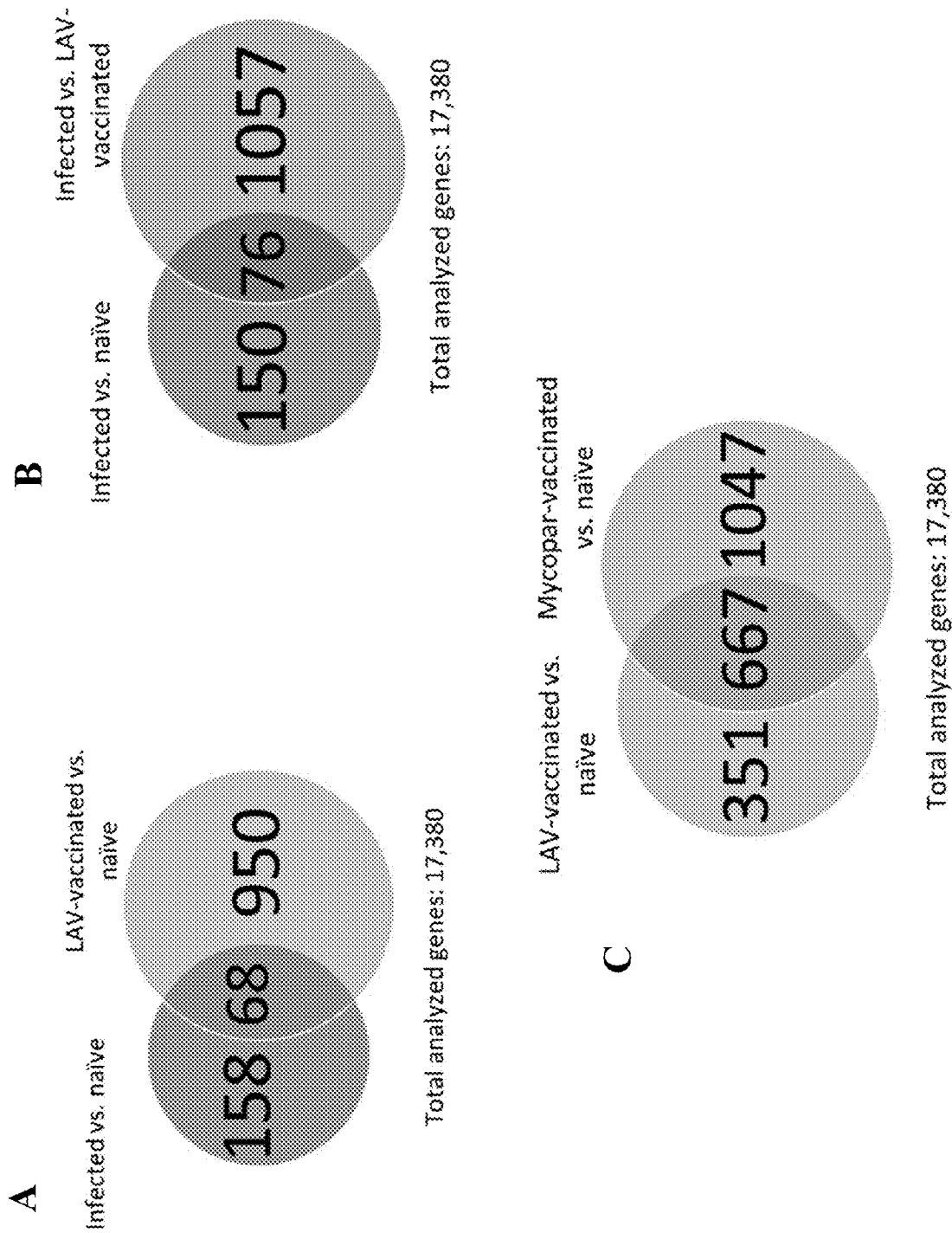
FIGS. 4A-4C show comparative transcriptome analysis of the infected and vaccinated goat groups. Venn diagrams show numbers of common DE transcripts between (A) the infected and vaccinated groups, each compared to the naïve group. (B) infected vs. naïve and infected vs. LAV-vaccinated groups and (C) LAV-vaccinated vs. naïve and Mycopar-vaccinated vs. naïve groups.
Figure 5:
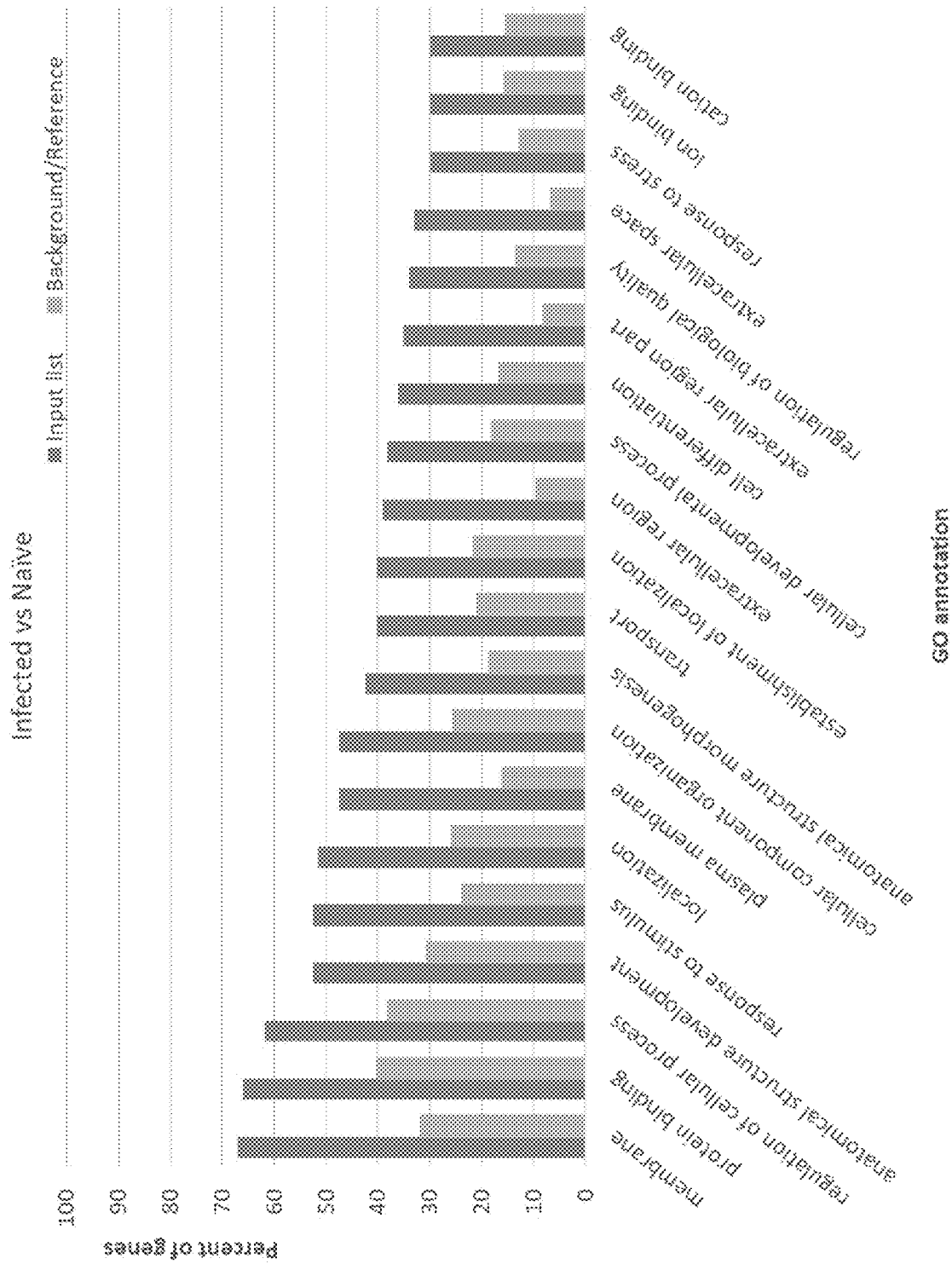
FIG. 5 shows significant terms in gene ontology analysis for the differentially expressed genes in infected goats compared to naïve control goats. The agriGO for automated identification of GO terms were used on the list of genes with significant differential expression when the transcriptomes of infected and naïve goats were compared.

Among those identified DE transcripts in the infected and LAV-vaccinated groups (each referenced against the naïve group), there were 68 transcripts in common (FIG. 4A). The majority of those transcripts were regulated in the same direction in both groups, but 11 transcripts were regulated in the opposite direction. A non-coding RNA transcript, LOC106503226 and a gene, PMP22, were the only two that were up-regulated 30 days PI and down-regulated 30 days post-vaccination. The remaining 9 transcripts (e.g. ART5 and IFNG) were down-regulated 30 days PI and up-regulated 30 days post-vaccination (Table 14). More comparative analysis of transcript profiles identified 76 transcripts commonly up- or down-regulated shared between the lists of genes from comparing infected vs. naïve control and M. paratuberculosis-infected vs. LAV-vaccinated transcripts (FIG. 4B). Those common genes could be considered the core responsive genes for M. paratuberculosis infection or vaccination with an LAV vaccine. For the inactivated vaccine, a total of 667 core genes were also regulated when compared to the LAV-vaccine group (Appendix F). Such core genes included those with potential rules in immunity (e.g. NOS2, RETN and IL21), another indication of core genes responsive to any M. paratuberculosis-specific vaccines whether live-attenuated or inactivated were used.

Figures 8A, 8B, 8C:
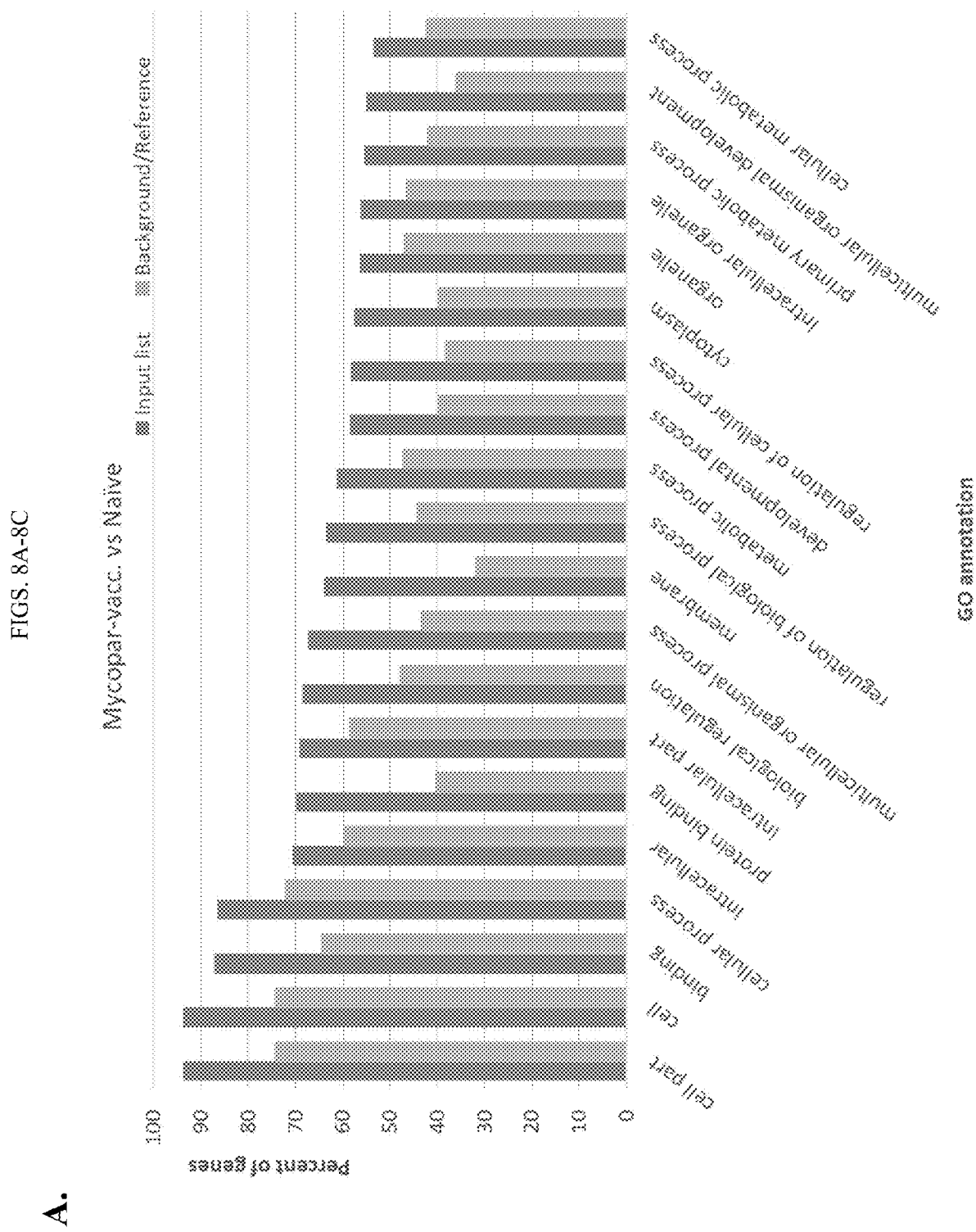
FIGS. 8A-8C show significant terms in gene ontology analysis, using agriGO, for the differentially expressed genes. The significant terms for the GO analysis for the Mycopar-vaccinated vs naïve group is shown in (A). Chart in (B) shows the significant terms for LAV-vaccinated vs naïve group and in (C) shows the significant terms for LAV-vaccinated vs. infected group. The significant GO terms for both comparisons are 1-binding, 2-intracellular, 3-intracellular part and 4-metabolic process.
Figures 8A, 8B, 8C:
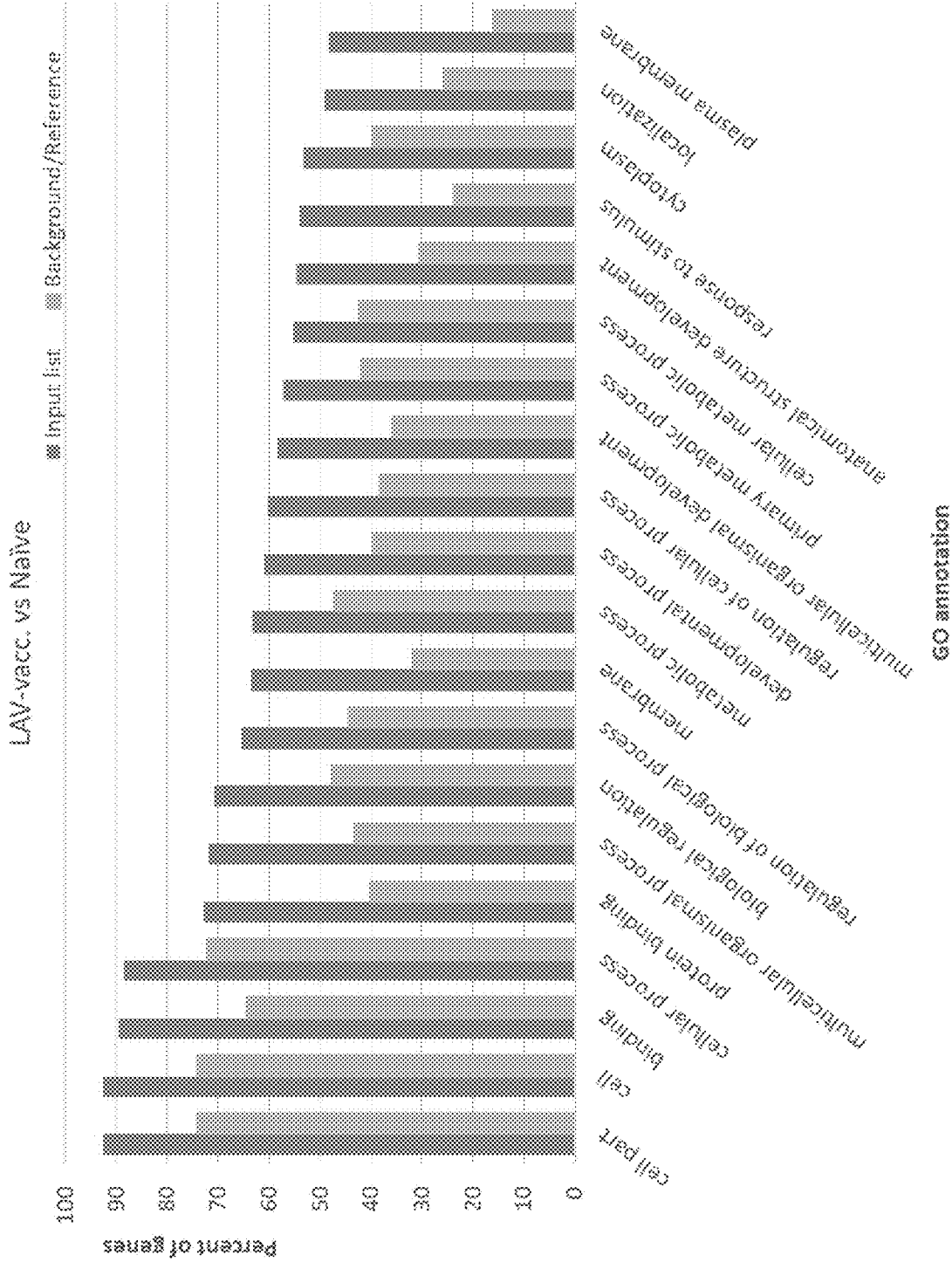
Figures 8A, 8B, 8C:
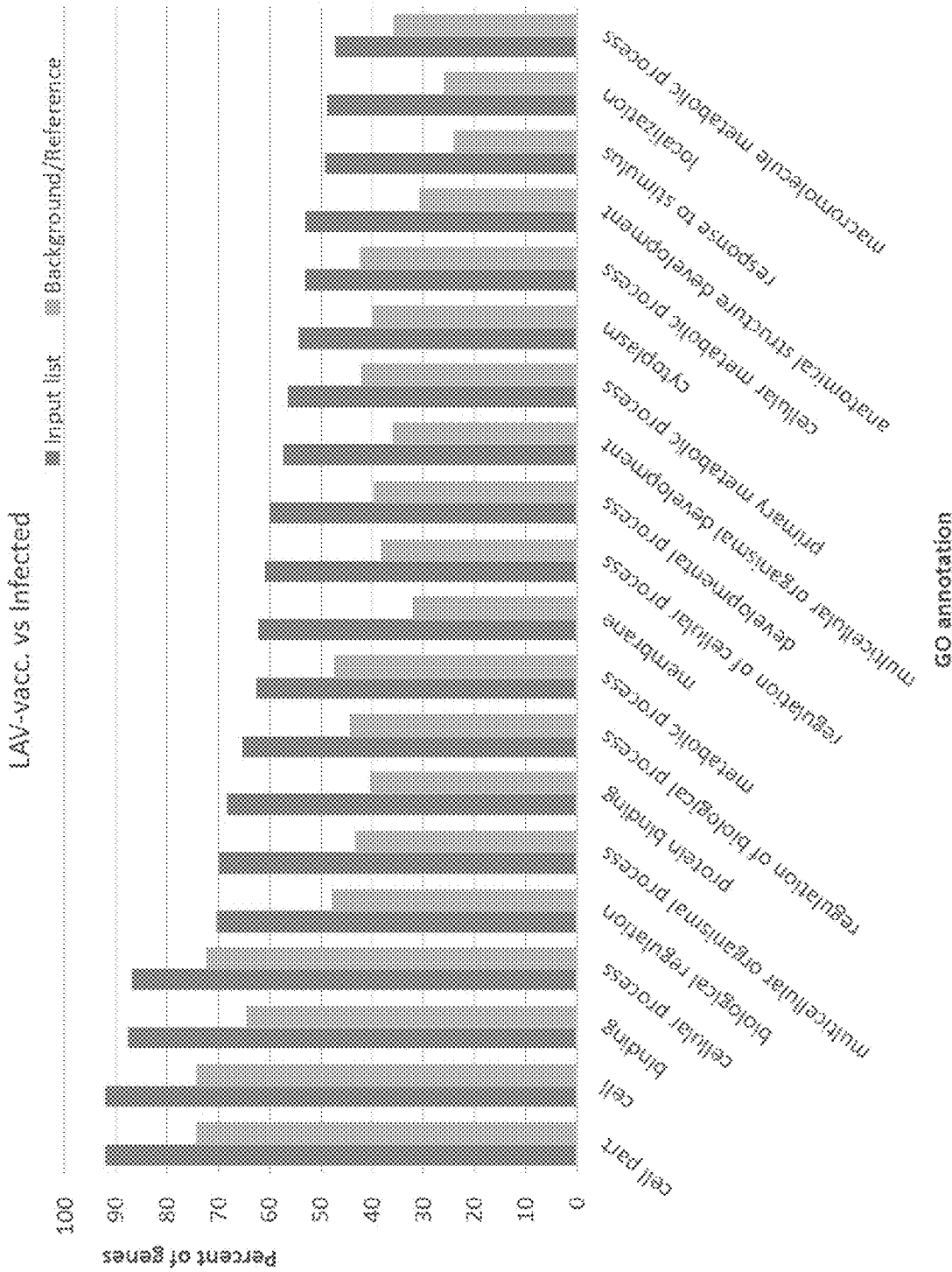

Pathways and networks of differentially expressed genes—To better define gene pathways involved in M. paratuberculosis infection, genes with significant differential expression were evaluated through gene ontology (GO) analysis using agriGO. This analysis provides categories of genes involved in different biological or molecular functions and those integral for different cellular components. Interestingly, the most abundant significant terms for the GO analysis for the infected vs naïve control group included genes involved in protein binding, regulation of cellular process and response to stimulus, which includes significant subcategories immune responses (GO:0006955) and inflammatory response (GO:0006954) (FIG. 3), suggesting the importance of controlling immune genes by M. paratuberculosis following infection. On the other hand, the largest gene groups with significant GO terms for the Mycopar®- or LAV-vaccinated vs infected groups included genes involved in binding, cellular process and metabolic process while those for the LAV-vaccinated vs infected group included genes involved in cellular process and biological regulation (FIGS. 8A-8C).

Figure 6A:
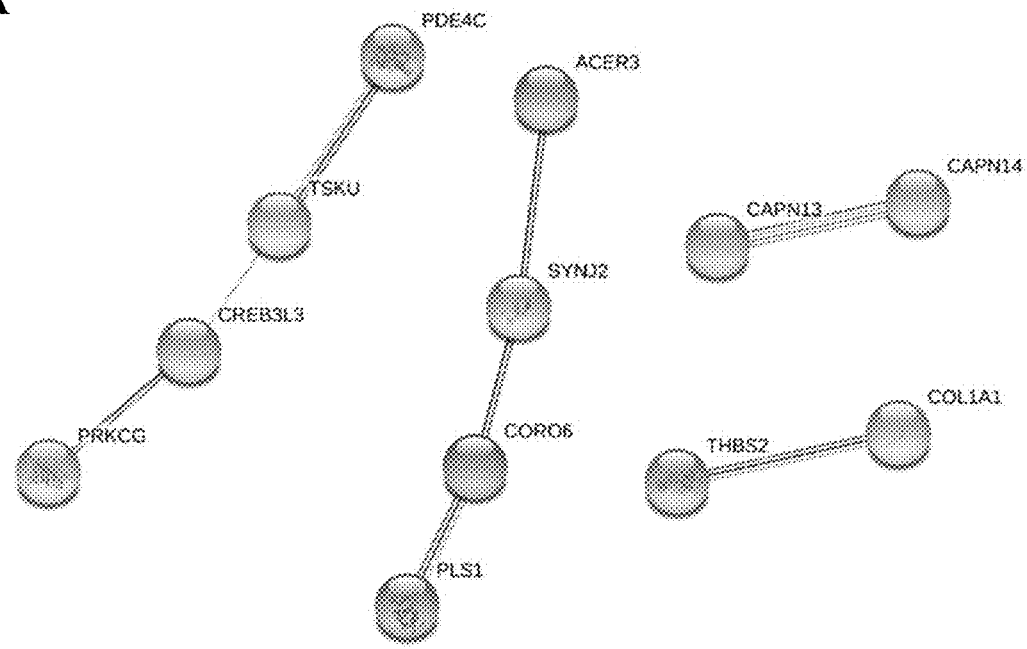
FIGS. 6A-6B show gene network analysis of DE genes in the infected group. (A) Genes that were significantly up-regulated. (B) Genes that were significantly down-regulated. IL-17A and IL-17F are two homologs in the IL-17 family. Light green lines represent connection between genes co-mentioned in an abstract in published studies, cyan lines represent putative pathway connections found in homologs in other species, black lines represent co-expression in *Bos taurus* or homologs in other species and pink lines represent experimentally determined association.
Figure 6B:
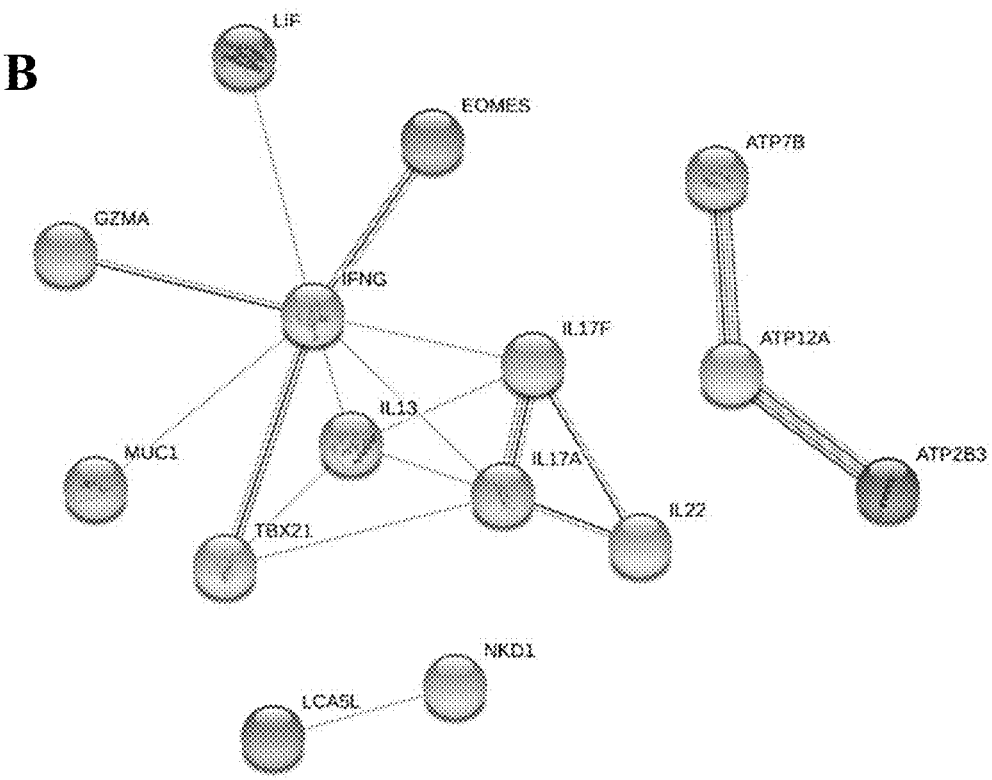

To better characterize gene networks activated during infection and vaccination, gene transcripts were further analyzed to identify co-regulated genes. FIGS. 6A-6B display gene network analysis in the post-infection group. Several in the up-regulated group of genes (FIG. 6A), such as ACER3, SYNJ2, CORO6 and PLS1, showed physical associations and co-expression among transcripts of the M. paratuberculosis-infected group. In addition, homologs of PDE4C and TSKU were also found associated (Halls and Cooper, 2010; Schlecht et al., 2012; Costanzo et al., 2016) and suggested to be involved in signaling and relaxin regulation (Halls and Cooper, 2010). In FIG. 6B, a co-down-regulation of ATP7B, ATP12A and ATP2B3 suggests a possible reduced activity of calcium transport in infected cells. This analysis also highlighted the negative regulation by M. paratuberculosis of host cytokines such as IFN-γ, IL-13, IL-17A, IL-17F and IL-22.

Prolonged Changes of Key Host Genes.

To further analyze the utility of transcriptome analysis for prediction of unique transcripts associated with infection or vaccination, we used real-time, quantitative PCR to compare transcript levels among animal groups over 12 months post-challenge (MPC) (FIGS. 7A-7D). Interestingly, IL-17 cytokine was repressed in the challenged and Mycopar® and LAV-vaccinated goats compared to the naïve control group for all examined times, except for the infected group at 2 MPC. Similarly, the Sept10 gene was induced, only at 2 MPC. On the other hand, IL-36 was activated soon after vaccination (1 and 2 MPC) but then repressed for the rest of the examined time points, i.e. 6 and 12 MPC. More interestingly, the IFN-γ expression profile was refractive to elicited immune responses. IFN-γ was induced soon in the LAV-vaccine group (1 MPC) but then continued to be expressed in the Mycopar®-vaccinated and M. paratuberculosis-challenged groups starting from 2 MPC until the end of the experiment. At all of these sampling times, the IFN-γ was consistently higher in the LAV-vaccine group compared to the challenged group.

Differential Expression in LAV vaccinated animals, Mycopar™ vaccinated animals, and infected animals.

TABLE 15

List of host genes (goat and cow) differentially expressed in both LAV and Mycopar vaccinated animals compared to infected animals

| Gene symbol | Gene ID | LAV vs. Infected Fold change | p-value | Mycopar vs Infected Fold change | p-value | Fold change difference | Description |
|---|---|---|---|---|---|---|---|
| STC1 | 102179386 | −4.668 | 1.4E−07 | −8.937 | 5.6E−17 | 4.268 | stanniocalcin 1 |
| NGF | 100862660 | −1.778 | 2.8E−02 | −5.001 | 1.2E−04 | 3.223 | nerve growth factor |
| FAM150B | 102183516 | −1.406 | 4.8E−02 | −4.355 | 2.0E−05 | 2.949 | family with sequence similarity 150 member B |
| FOXE1 | 106502413 | −1.679 | 1.4E−02 | −4.290 | 4.5E−07 | 2.611 | forkhead box E1 |
| C28H10orf71 | 102181364 | −2.870 | 5.2E−03 | −5.463 | 1.3E−04 | 2.593 | chromosome 28 C10orf71 homolog |
| HEBP2 | 102174123 | −1.584 | 4.2E−02 | −4.133 | 1.9E−03 | 2.549 | heme binding protein 2 |
| IL11 | 102184367 | −2.218 | 8.9E−03 | −4.659 | 1.1E−05 | 2.440 | interleukin 11 |
| KRT82 | 102183763 | −1.630 | 5.6E−03 | −3.951 | 4.0E−04 | 2.320 | keratin 82 |
| NTNG1 | 102190191 | −1.704 | 8.1E−06 | −3.726 | 7.9E−16 | 2.022 | netrin G |
| SORCS2 | 102176511 | −1.357 | 4.9E−03 | −3.365 | 5.8E−09 | 2.008 | sortilin related VPS10 domain containing receptor 2 |
| HS3ST2 | 102183286 | −3.638 | 1.0E−07 | −1.432 | 3.4E−02 | −2.206 | heparan sulfate-glucosamine 3-sulfotransferase 2 |
| TGFB3 | 102189962 | 2.706 | 8.5E−03 | 5.103 | 4.2E−06 | −2.397 | transforming growth factor beta 3 |

TABLE 16

List of host genes (goat and cow) differentially expressed in LAV vaccinated animals compared to infected animals but not differentially expressed in Mycopar® vaccinated animals compared to infected animals.

| Gene symbol | Gene ID | LAV vs. Infected Fold change | p-value | Mycopar vs Infected Fold change | p-value | Description |
|---|---|---|---|---|---|---|
| LOC102176439 | 102176439 | 3.865 | 0.003 | 0.763 | 0.603 | misc_RNA |
| LOC102187130 | 102187130 | 3.341 | 0.002 | −0.300 | 0.800 | protein ARMCX6-like |
| LOC108633178 | 108633178 | 2.976 | 0.000 | 0.895 | 0.129 | granzyme B-like |
| CPNE6 | 102180500 | 2.755 | 0.000 | 0.841 | 0.289 | copine 6 |
| IL13 | 102187477 | 2.752 | 0.000 | −0.220 | 0.752 | interleukin 13 |
| CCR10 | 102184001 | 2.581 | 0.007 | 0.700 | 0.502 | C-C motif chemokine receptor 10 |
| C1QL2 | 102176742 | 2.427 | 0.032 | −0.520 | 0.684 | complement C1q like 2 |
| MGAT3 | 102185445 | 2.418 | 0.005 | −0.570 | 0.553 | mannosyl (beta-4-)-glycoprotein beta-4-N-acetylglucosaminyltransferase |
| GNLY | 102191341 | 2.212 | 0.000 | 0.807 | 0.146 | granulysin transcript |
| KY | 102169426 | −3.013 | 0.003 | −0.144 | 0.884 | kyphoscoliosis peptidase |
| RAET1E | 108636743 | −3.784 | 0.002 | −0.895 | 0.497 | retinoic acid early transcript 1E |

TABLE 17

List of host genes (goats and cow) differentially expressed in Mycopar ® vaccinated animals compared to infected animals but not differentially expressed in LAV vaccinated animals compared to infected animals.

| Gene symbol | Gene ID | LAV vs. Infected | | Mycopar vs Infected | | Description |
|---|---|---|---|---|---|---|
| | | Fold change | p-value | Fold change | p-value | |
| LOC102174895 | 102174895 | 1.762 | 0.141 | 5.278 | 0.000 | vascular cell adhesion protein |
| BMP10 | 102185577 | 0.557 | 0.721 | 4.192 | 0.012 | bone morphogenetic protein 10 |
| CXCL12 | 102169556 | −0.755 | 0.302 | 3.613 | 0.000 | C-X-C motif chemokine ligand 12 |
| LOC108633303 | 108633303 | −0.272 | 0.769 | 2.659 | 0.008 | platelet glycoprotein 4-like |
| PPARG | 100861309 | 0.904 | 0.053 | 2.339 | 0.000 | peroxisome proliferator activated receptor gamma |
| F13A1 | 102169238 | −0.132 | 0.883 | 2.239 | 0.021 | coagulation factor XIII A chain |
| LOC108634012 | 108634012 | −0.173 | 0.804 | −2.736 | 0.000 | homeobox protein MSX-3-like |
| LRRC3 | 102188902 | 0.357 | 0.786 | −2.907 | 0.042 | leucine rich repeat containing 3 |
| MYO10 | 102175716 | −0.967 | 0.023 | −3.183 | 0.000 | myosin X |
| LOC102179419 | 102179419 | −0.471 | 0.759 | −3.435 | 0.040 | myeloid-associated differentiation marker |

Discussion

Infection with *M. paratuberculosis* is costing the dairy industry significant economic losses (Cho et al., 2012) and is difficult to detect its presence, especially during early disease stages (Li et al., 2017). In this project, the goat PBMC transcriptome was profiled using RNA-Sequencing (RNA-Seq) to compare the early gene expression, 30 days post-infection and post-vaccination, compared to healthy, naïve controls. In addition to better understanding of disease progression, such analysis is expected to yield targets for further development into a diagnostic assay for early stages of Johne's disease. Many transcriptomic analyzing tools largely depend on information from an annotated genome. In this study, our quality of transcriptomic analyses improved as the goat genome assembly was significantly refined (Bickhart et al., 2017). According to NCBI *Capra hircus* Annotation Release 102, of 20,593 predicted coding genes, 20,256 had a protein aligned 50% or more of the query against the UniProtKB/Swiss-Prot curated proteins (NCBI, 2016). The updated annotation thus provides a much more reliable reference to our analysis. The generated RNA-Seq dataset could also benefit further improvement of goat genome annotation. As expected, a large number of differentially expressed (DE) transcripts were found between the vaccinated and infected groups (1133 genes) and between the vaccinated and naïve control group (1018 genes). In contrast, there was a relatively small number (226) of DE transcripts when comparing the infected and naïve control group. This large difference in the number of DE transcripts is most likely associated with the route of administration since both vaccines were administered subcutaneously (contrary to oral infection), allowing for increased contact with PBMCs in the bloodstream, while challenge dose of *M. paratuberculosis* could reach PBMC following intestinal invasion (Stabel et al., 2009). Our analysis, further illustrated the importance of route of infection and/or vaccination for the type and magnitude of the generated host responses.

Although the comparison between the infected and naïve control group produced a relatively small number of DE transcripts, preliminary evaluation of these genes indicated a large number of genes with immunological and inflammatory functions, including interferon gamma (IFN-γ), IL-18 binding protein, IL-17A, and IL-22. IFN-γ is an important player in the defense against intracellular pathogens including mycobacteria (Arsenault et al., 2012). A previous study in cattle showed that in the subclinical stages of infection, IFN-γ expression increased at the site of infection (Sweeney et al., 1998). Other studies indicate that *M. paratuberculosis*-infected animals produce IFN-γ but are unresponsive to it (Arsenault et al., 2012). In that study, IFN-γ was secreted significantly less (−3.36 fold change) in subclinically infected goats compared with the naïve, control goats. This IFN-γ profile was also evident in subclinically infected goats vs vaccinated goats (−13.0 fold change). Previously, IFN-γ was reported to be induced in PBMC's stimulated with *M. paratuberculosis* whole-cell sonicate from subclinically infected cows (Stabel, 2000). However, these cows ranged from 2-10 years of age and therefore were much further along in the infection pathogenesis than in the current study, which tested goats 30 days PI. The host response clearly changes over time and this data may demonstrate that. Potentially linked to the identified repression of IFN-γ, is the moderate up-regulation (+1.30 fold change) of interleukin 18 binding protein (IL-18 bp) in the infected vs naïve control group. IL-18 bp binds to IL-18 to block its biological activity (Novick et al., 1999). IL-18 is a pro-inflammatory cytokine that functions in the early Th1 cytokine response and induces IFN-γ production. A major source of IL-18 bp is from intestinal endothelial cells and macrophages (Corbaz et al., 2002). Therefore, IL-18 bp serves to modulate the early Th1 immune response in the intestine, the site of *M. paratuberculosis* infection. Interestingly, IL-18 bp has been found to be up-regulated during active Crohn's disease, an inflammatory bowel disease in humans with potential association to *M. paratuberculosis* infection (Corbaz et al., 2002).

As expected, genes involved in immune responses (e.g. LIF, IFN-γ and IL-22), were found to be DE among examined goat groups. LIF is a pleiotropic cytokine belonging to the IL-6 cytokine family with receptors primarily on monocytes/macrophages (Nicola and Babon, 2015). In the infected group, both LIF and IL-22, a Th17-related cytokine, were down-regulated in the infected group vs the control or the vaccinated groups. These three genes, along with IL-13 and IL-17, were also found having associations in the protein network analysis. IL-17 was also down-regulated in the infected vs control group. Down-regulation of IFN-γ, IL-22 and IL-17 genes may suggest overall down-regulation of Th1 and Th17 cell activities and reduced cellular immunity against infections. Several studies in *Mycobacterium tuberculosis* and *Mycobacterium bovis* have shown significant IL-17 responses (Blanco et al., 2011; Jurado et al., 2012). A recent study on RNA-Seq analysis in cattle infected with *M. bovis* showed an up-regulation of IL-17, IL-22, and IFN-γ at one-month PI (Waters et al., 2015). This is in contrast to some of our findings in the present study (in case of IL-17) which was further confirmed by prolonged analysis of key genes up to 12 months post infection (FIGS. 7A-7D). Such difference could be attributed to the difference in host response to *M. bovis* vs. *M. paratuberculosis*. Further investigation into these key immune regulated genes as will aid in understanding how the host is dynamically responding to *M. paratuberculosis* infection or vaccination.

Figures 7A, 7B, 7C, 7D:
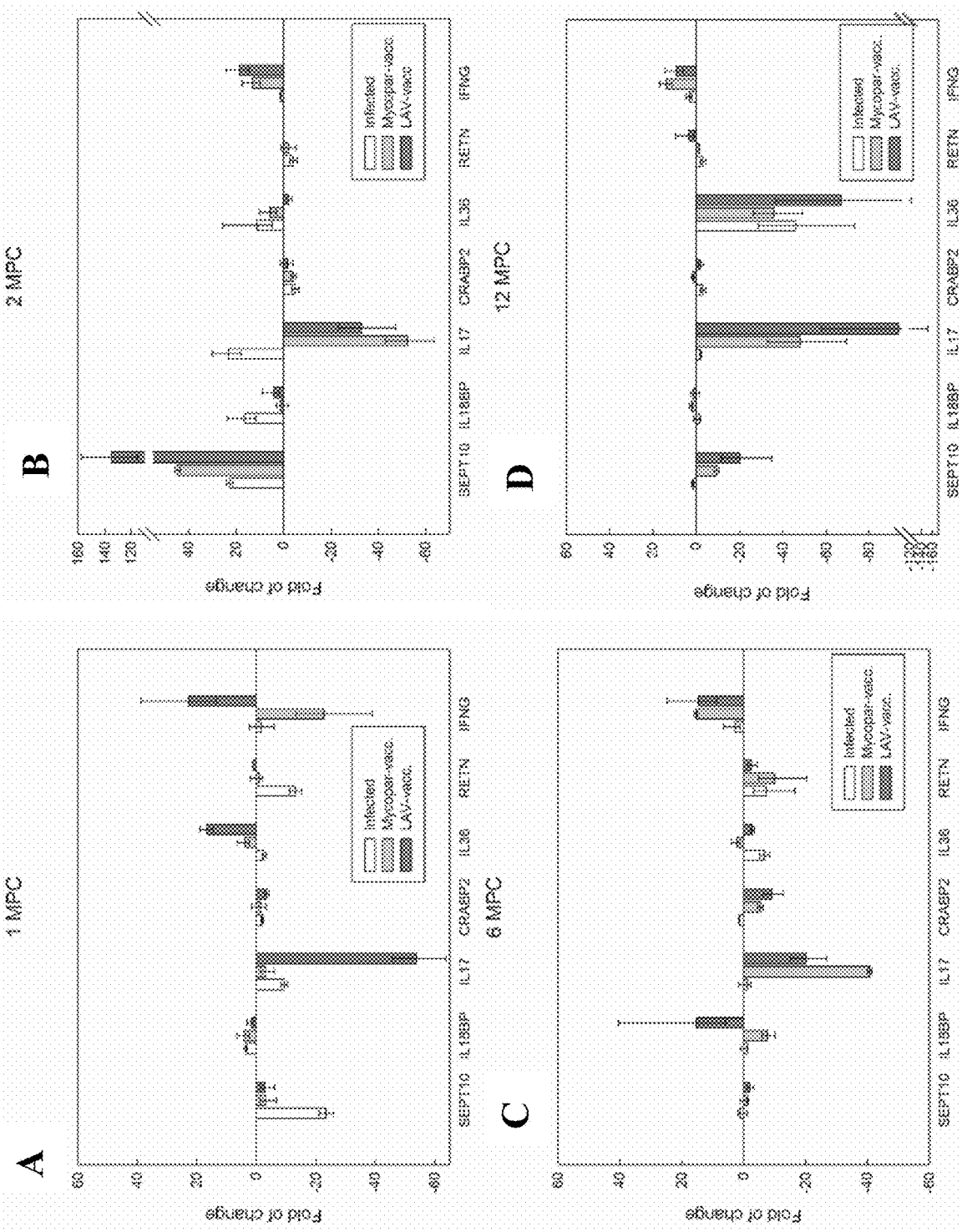
FIGS. 7A-7D show the transcriptional profile of key caprine genes over 12 months post challenge with *M. paratuberculosis*. Panels display quantitative real-time PCR analysis of total RNA extracted from blood samples collected from goat groups at 1 (A), 2 (B), 6 (C) and 12 (D) months post challenge (MPC). Expression levels were calculated with ΔΔCt relative quantitation method relative to the GAPDH gene expression in the naïve group. Target gene names are listed below each panel and fold change for the infected, Mycopar® or LAV-vaccinated relative to naïve goat groups are listed on the Y-axis. At each time point, samples from three animals in each group except the infected group at 1 MPC (N=2) were included and standard errors of the mean (SEM) of the three measurements were presented as error bars.

Our gene network analysis also shows associations among genes that were up-regulated in the infected group (FIG. 7A). Interestingly, homologs of ACER3, SYNJ2, CORO6 and PLS1 in animal species other than goats (mainly bovine, *Bos Taurus*) were also shown to have physical associations (Schlecht et al., 2012; Hein et al., 2015) and co-expression (Clancy et al., 2003; Janji et al., 2010) as well. Particularly, homologs of CORO6, an actin binding protein, was suggested to be involved in cytokinesis. In *M. tuberculosis*-infected macrophages, CORO6 homolog coronin-1a was suggested to inhibit auto-phagosome formation and facilitate *M. tuberculosis* survival (Seto et al., 2012). In addition, homologs of PDE4C and TSKU were also found associated (Halls and Cooper, 2010; Schlecht et al., 2012; Costanzo et al., 2016) and suggested to be involved in signaling and relaxin regulation (Halls and Cooper, 2010). It may thus imply a status of progression of an *M. paratuberculosis* infection in hosts as observed in *M. tuberculosis* infection (Seto et al., 2012). This observation, along with the likely reduced cellular immunity discussed above, is consistent with the infection status of the host. It is unclear, however, how bacterial or host factors regulate the expression of those genes. Understanding the host-pathogen interaction early in infection will allow for the identification of genes upregulated during initial infection. A useful biomarker for infection must be specific, detectable over the course of the disease with varying inoculation doses, and easily measurable. Moreover, it would improve interpretation of early disease detection if the biomarkers could differentiate infected and vaccinated animals. In our analyses, we identified 9 transcripts (out of 11 in Table 14) that were down-regulated 30 days PI and up-regulated 30 days post-vaccination. This biphasic regulation of those genes or transcripts might make them specific markers for differentiating vaccinated animals that are healthy or those infected with *M. paratuberculosis*.

The RNA-Seq analysis was performed only on samples taken one month post-infection or post-vaccination to identify early gene regulations in tested groups, notably, between one month after vaccinated only and infected only groups. This comparison differentiates host gene regulating responses after exposure to vaccine strains or virulent strains of *M. paratuberculosis*. The vaccinated animals were then challenged two months after the vaccination and several key gene expressions were profiled with quantitative PCR (FIGS. 7A-7D). The temporal expression patterns within the tested one year period could reflect unique characteristics of host responses after exposure to virulent *M. paratuberculosis* with or without prior vaccinations and could also benefit development of diagnostics. For example, IL-17 expressions in the vaccinated animals remained highly repressed at all time while peaking at 2 month post-challenge in the infected only group.

---

We claim:

1. A method comprising the steps of:
   a) obtaining a blood sample from a mammal, wherein the mammal is a ruminant;
   b) measuring the expression level of FAM198B and AOAH in the blood sample by quantitative polymerase chain reaction (qPCR);
   c) administering a live-attenuated or inactivated *Mycobacterium* vaccine to the mammal having equal relative expression of AOAH and FAM198B in the sample or having relative expression of AOAH and FAM198B within error of the qPCR used to measure the expression level of AOAH and FAM198b in the sample.

2. The method of claim 1, wherein the mammal is selected from the group consisting of cow and goat.

3. The method of claim 1, wherein the vaccine is a *mycobacterium* mutant vaccine.

4. The method of claim 3, wherein the *mycobacterium* mutant vaccine comprises at least one mutation in at least one gene sequence encoding global gene regulators (GGRs) selected from the group consisting of sigH, sigL and LipN.

5. The method of claim 1, wherein mammal is not actively shedding mycobacteria.

6. The method of claim 1, wherein the mammal has a negative mycobacteria antibody test.

7. A method comprising the steps of
   a) obtaining a blood sample from a mammal, wherein the mammal is a ruminant;
   b) measuring the expression level of at least two biomarkers consisting of FAM198B and AOAH in the blood sample by quantitative polymerase chain reaction (qPCR);
   c) administering antibiotics to the mammal having higher relative expression of FAM198B than AOAH to treat the mammal for a mycobacterial infection.

8. The method of claim 7, wherein the mammal is selected from the group consisting of cow and goat.

9. The method of claim 7, wherein the mammal is not actively shedding mycobacteria.

10. The method of claim 7, wherein the mammal has a negative mycobacteria antibody test.

* * * * *

SEQUENCE LISTING

```
<160> NUMBER OF SEQ ID NOS: 35

<210> SEQ ID NO 1
<211> LENGTH: 373
<212> TYPE: PRT
<213> ORGANISM: Mycobacterium paratuberculosis

<400> SEQUENCE: 1

Met Thr Lys Pro Leu Thr Asp Thr Ala Pro Val Asp Pro Gly Ala Gln
1               5                   10                  15

Arg Gly Ser Met Pro Leu Thr Asn Arg Ile Gln Gly Ala Val Thr Ser
            20                  25                  30

Val Gly Val Lys Val Ile Pro Trp Ile Pro Thr Ala Val Arg Arg Gly
        35                  40                  45

Leu Val Arg Gly Arg Ser Val Ile Ile Asp Gly Asn Thr Leu Asp Pro
    50                  55                  60

Thr Leu Gln Leu Met Leu Ser Gly Leu Arg Ala Val Gly Ile Asp Gly
65                  70                  75                  80

Leu Val Val Asp Asp Asp Pro Glu Leu Ser Arg Ala Gln Met His Glu
                85                  90                  95

Ser Thr Val Gly Phe Pro Gly Pro Gln Ile His Val Asp Val Ala Glu
            100                 105                 110
```

Leu Ala Leu Pro Gly Pro Ala Gly Asp Ile Pro Ala Arg His Tyr Arg
            115                 120                 125

Pro Ala Gly Gly Glu Thr Gln Ala Pro Leu Leu Val Phe Tyr His Gly
        130                 135                 140

Gly Gly Trp Ser Ile Gly Asp Leu Asp Thr His Asp Ser Leu Cys Arg
145                 150                 155                 160

Leu Thr Cys Arg Asp Ala Gly Ile His Val Leu Ser Ile Asp Tyr Arg
                165                 170                 175

Leu Ala Pro Glu His Pro Ala Pro Ala Ile Asp Asp Ala Tyr Ala
            180                 185                 190

Ala Phe Thr Trp Ala His Glu His Ala Gly Glu Leu Gly Ala Ile Pro
        195                 200                 205

Gly Arg Val Ala Val Gly Gly Asp Ser Ala Gly Gly Asn Leu Ala Ala
210                 215                 220

Val Val Ser Gln Leu Ala Arg Asp Ala Gly Gly Pro Ala Pro Val Leu
225                 230                 235                 240

Gln Trp Leu Ile Tyr Pro Arg Thr Asp Phe Thr Ala Arg Thr Arg Ser
                245                 250                 255

Leu Ser Leu Phe Ser Arg Gly Phe Leu Leu Thr Lys Arg Asp Ile Asp
            260                 265                 270

Trp Phe Glu Ser Gln Tyr Leu Arg Asn Ser Arg Leu Asp Arg Thr Asp
        275                 280                 285

Pro Arg Val Ser Pro Ala Leu Ala Glu Ser Leu Ala Gly Leu Ala Pro
290                 295                 300

Ala Leu Ile Ala Val Ala Gly Phe Asp Pro Leu Arg Asp Glu Gly Gln
305                 310                 315                 320

Ser Tyr Ala Glu Ala Leu Arg Ala Ala Gly Thr Pro Val Asp Leu Arg
                325                 330                 335

Tyr Leu Gly Ser Leu Thr His Gly Phe Ala Asn Leu Phe Gln Leu Gly
            340                 345                 350

Gly Asp Ser Met Val Ala Thr Ser Glu Leu Ile Ser Ala Leu Arg Ala
        355                 360                 365

His Leu Ser Arg Val
    370

<210> SEQ ID NO 2
<211> LENGTH: 376
<212> TYPE: PRT
<213> ORGANISM: Mycobacterium bovis

<400> SEQUENCE: 2

Met Thr Lys Ser Leu Pro Gly Val Ala Asp Leu Arg Leu Gly Ala Asn
1               5                   10                  15

His Pro Arg Met Trp Thr Arg Arg Val Gln Gly Thr Val Val Asn Val
            20                  25                  30

Gly Val Lys Val Leu Pro Trp Ile Pro Thr Pro Ala Lys Arg Ile Leu
        35                  40                  45

Ser Ala Gly Arg Ser Val Ile Ile Asp Gly Asn Thr Leu Asp Pro Thr
    50                  55                  60

Leu Gln Leu Met Leu Ser Thr Ser Arg Ile Phe Gly Val Asp Gly Leu
65                  70                  75                  80

Ala Val Asp Asp Asp Ile Val Ala Ser Arg Ala His Met Arg Ala Ile
                85                  90                  95

Cys Glu Ala Met Pro Gly Pro Gln Ile His Val Asp Val Thr Asp Leu
            100                 105                 110

Ser Ile Pro Gly Pro Ala Gly Glu Ile Pro Ala Arg His Tyr Arg Pro
            115                 120                 125

Ser Gly Gly Ala Thr Pro Leu Leu Val Phe Tyr His Gly Gly Gly
        130                 135                 140

Trp Thr Leu Gly Asp Leu Asp Thr His Asp Ala Leu Cys Arg Leu Thr
145                 150                 155                 160

Cys Arg Asp Ala Asp Ile Gln Val Leu Ser Ile Asp Tyr Arg Leu Ala
                165                 170                 175

Pro Glu His Pro Ala Pro Ala Val Glu Asp Ala Tyr Ala Ala Phe
            180                 185                 190

Val Trp Ala His Glu His Ala Ser Asp Glu Phe Gly Ala Leu Pro Gly
            195                 200                 205

Arg Val Ala Val Gly Gly Asp Ser Ala Gly Gly Asn Leu Ser Ala Val
        210                 215                 220

Val Cys Gln Leu Ala Arg Asp Lys Ala Arg Tyr Glu Gly Gly Pro Thr
225                 230                 235                 240

Pro Val Leu Gln Trp Leu Leu Tyr Pro Arg Thr Asp Phe Thr Ala Gln
                245                 250                 255

Thr Arg Ser Met Gly Leu Phe Gly Asn Gly Phe Leu Leu Thr Lys Arg
            260                 265                 270

Asp Ile Asp Trp Phe His Thr Gln Tyr Leu Arg Asp Ser Asp Val Asp
            275                 280                 285

Pro Ala Asp Pro Arg Leu Ser Pro Leu Leu Ala Glu Ser Leu Ser Gly
        290                 295                 300

Leu Ala Pro Ala Leu Ile Ala Val Ala Gly Phe Asp Pro Leu Arg Asp
305                 310                 315                 320

Glu Gly Glu Ser Tyr Ala Lys Ala Leu Arg Ala Ala Gly Thr Ala Val
                325                 330                 335

Asp Leu Arg Tyr Leu Gly Ser Leu Thr His Gly Phe Leu Asn Leu Phe
            340                 345                 350

Gln Leu Gly Gly Gly Ser Ala Ala Gly Thr Asn Glu Leu Ile Ser Ala
        355                 360                 365

Leu Arg Ala His Leu Ser Arg Val
        370                 375

```
<210> SEQ ID NO 3
<211> LENGTH: 378
<212> TYPE: PRT
<213> ORGANISM: Artificial Sequence
<220> FEATURE:
<223> OTHER INFORMATION: synthetic consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
```

-continued

```
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (44)..(46)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (87)..(89)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(101)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (114)..(115)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (133)..(134)
```

```
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (148)..(149)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (187)..(188)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (262)..(263)
<223> OTHER INFORMATION: Xaa can be any naturally occurring amino acid
<220> FEATURE:
<221> NAME/KEY: misc_feature
<222> LOCATION: (266)..(267)
<223> OTHER INFORMATION: Xaa can be any naturally occurring amino acid
<220> FEATURE:
<221> NAME/KEY: misc_feature
<222> LOCATION: (280)..(281)
<223> OTHER INFORMATION: Xaa can be any naturally occurring amino acid
<220> FEATURE:
<221> NAME/KEY: misc_feature
```

```
<222> LOCATION: (286)..(286)
<223> OTHER INFORMATION: Xaa can be any naturally occurring amino acid
<220> FEATURE:
<221> NAME/KEY: misc_feature
<222> LOCATION: (288)..(289)
<223> OTHER INFORMATION: Xaa can be any naturally occurring amino acid
<220> FEATURE:
<221> NAME/KEY: misc_feature
<222> LOCATION: (291)..(292)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (361)..(363)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid

<400> SEQUENCE: 3

Met Thr Lys Xaa Leu Xaa Xaa Xaa Ala Xaa Xaa Xaa Xaa Gly Ala Xaa
1               5                   10                  15

Xaa Xaa Xaa Met Pro Xaa Thr Xaa Arg Xaa Gln Gly Xaa Val Xaa Xaa
            20                  25                  30

Val Gly Val Lys Val Xaa Pro Trp Ile Pro Thr Xaa Xaa Xaa Arg Xaa
        35                  40                  45

Leu Xaa Xaa Gly Arg Ser Val Ile Ile Asp Gly Asn Thr Leu Asp Pro
    50                  55                  60

Thr Leu Gln Leu Met Leu Ser Xaa Xaa Arg Xaa Xaa Gly Xaa Asp Gly
65                  70                  75                  80

Leu Xaa Val Asp Asp Asp Xaa Xaa Xaa Ser Arg Ala Xaa Met Xaa Xaa
                85                  90                  95

Xaa Xaa Xaa Xaa Xaa Pro Gly Pro Gln Ile His Val Asp Val Xaa Xaa
            100                 105                 110

Leu Xaa Xaa Pro Gly Pro Ala Gly Xaa Ile Pro Ala Arg His Tyr Arg
    115                 120                 125

Pro Xaa Gly Gly Xaa Xaa Gln Xaa Pro Leu Leu Val Phe Tyr His Gly
        130                 135                 140
```

```
Gly Gly Trp Xaa Xaa Gly Asp Leu Asp Thr His Asp Xaa Leu Cys Arg
145                 150                 155                 160

Leu Thr Cys Arg Asp Ala Xaa Ile Xaa Val Leu Ser Ile Asp Tyr Arg
                165                 170                 175

Leu Ala Pro Glu His Pro Ala Pro Ala Ala Xaa Xaa Asp Ala Tyr Ala
            180                 185                 190

Ala Phe Xaa Trp Ala His Glu His Ala Xaa Asp Glu Xaa Gly Ala Xaa
        195                 200                 205

Pro Gly Arg Val Ala Val Gly Gly Asp Ser Ala Gly Gly Asn Leu Xaa
    210                 215                 220

Ala Val Val Xaa Gln Leu Ala Arg Asp Xaa Ala Arg Tyr Glu Gly Gly
225                 230                 235                 240

Pro Xaa Pro Val Leu Gln Trp Leu Xaa Tyr Pro Arg Thr Asp Phe Thr
        245                 250                 255

Ala Xaa Thr Arg Ser Xaa Xaa Leu Phe Xaa Xaa Gly Phe Leu Leu Thr
        260                 265                 270

Lys Arg Asp Ile Asp Trp Phe Xaa Xaa Gln Tyr Leu Arg Xaa Ser Xaa
        275                 280                 285

Xaa Asp Xaa Xaa Asp Pro Arg Xaa Ser Pro Xaa Leu Ala Glu Ser Leu
290                 295                 300

Xaa Gly Leu Ala Pro Ala Leu Ile Ala Val Ala Gly Phe Asp Pro Leu
305                 310                 315                 320

Arg Asp Glu Gly Xaa Ser Tyr Ala Xaa Ala Leu Arg Ala Ala Gly Thr
                325                 330                 335

Xaa Val Asp Leu Arg Tyr Leu Gly Ser Leu Thr His Gly Phe Xaa Asn
            340                 345                 350

Leu Phe Gln Leu Gly Gly Xaa Ser Xaa Xaa Xaa Thr Xaa Glu Leu Ile
            355                 360                 365

Ser Ala Leu Arg Ala His Leu Ser Arg Val
    370                 375

<210> SEQ ID NO 4
<211> LENGTH: 17
<212> TYPE: DNA
<213> ORGANISM: Artificial Sequence
<220> FEATURE:
<223> OTHER INFORMATION: synthetic

<400> SEQUENCE: 4
ggtgagcgcc agaggaa                                                  17

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
cagcttctcc tcttggtgga c                                             21

<210> SEQ ID NO 6
<211> LENGTH: 18
<212> TYPE: DNA
<213> ORGANISM: Artificial Sequence
<220> FEATURE:
<223> OTHER INFORMATION: synthetic

<400> SEQUENCE: 6
```

```
aactggatcc cagacccc                                                     18

<210> SEQ ID NO 7
<211> LENGTH: 17
<212> TYPE: DNA
<213> ORGANISM: Artificial Sequence
<220> FEATURE:
<223> OTHER INFORMATION: synthetic

<400> SEQUENCE: 7
gtagctgctg ggagcgc                                                      17

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
ggaacacgaa ctccagaagg c                                                 21

<210> SEQ ID NO 9
<211> LENGTH: 23
<212> TYPE: DNA
<213> ORGANISM: Artificial Sequence
<220> FEATURE:
<223> OTHER INFORMATION: synthetic

<400> SEQUENCE: 9
acagagttca tgtgatggtc cac                                               23

<210> SEQ ID NO 10
<211> LENGTH: 17
<212> TYPE: DNA
<213> ORGANISM: Artificial Sequence
<220> FEATURE:
<223> OTHER INFORMATION: synthetic

<400> SEQUENCE: 10
accaccgtgc gtaccac                                                      17

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
ggaggtcttg ggaccctctc                                                   20

<210> SEQ ID NO 12
<211> LENGTH: 26
<212> TYPE: DNA
<213> ORGANISM: Artificial Sequence
<220> FEATURE:
<223> OTHER INFORMATION: synthetic

<400> SEQUENCE: 12
cgttaatagc agttccttct agcaac                                            26

<210> SEQ ID NO 13
<211> LENGTH: 22
<212> TYPE: DNA
```

```
<213> ORGANISM: Artificial Sequence
<220> FEATURE:
<223> OTHER INFORMATION: synthetic

<400> SEQUENCE: 13
ggatagccct ggatttctgt gc                                                 22

<210> SEQ ID NO 14
<211> LENGTH: 22
<212> TYPE: DNA
<213> ORGANISM: Artificial Sequence
<220> FEATURE:
<223> OTHER INFORMATION: synthetic

<400> SEQUENCE: 14
tgaggcagta aggaacattg gc                                                 22

<210> SEQ ID NO 15
<211> LENGTH: 17
<212> TYPE: DNA
<213> ORGANISM: Artificial Sequence
<220> FEATURE:
<223> OTHER INFORMATION: synthetic

<400> SEQUENCE: 15
agtccatgcc tgcgcac                                                       17

<210> SEQ ID NO 16
<211> LENGTH: 21
<212> TYPE: DNA
<213> ORGANISM: Artificial Sequence
<220> FEATURE:
<223> OTHER INFORMATION: synthetic

<400> SEQUENCE: 16
gcagctctga gaaactggag g                                                  21

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
tccggcctcg aaagagattc t                                                  21

<210> SEQ ID NO 18
<211> LENGTH: 23
<212> TYPE: DNA
<213> ORGANISM: Artificial Sequence
<220> FEATURE:
<223> OTHER INFORMATION: synthetic

<400> SEQUENCE: 18
ggcgtgaacc acgagaagta taa                                                23

<210> SEQ ID NO 19
<211> LENGTH: 18
<212> TYPE: DNA
<213> ORGANISM: Artificial Sequence
<220> FEATURE:
<223> OTHER INFORMATION: synthetic

<400> SEQUENCE: 19
ggcagtgatg gcgtggac                                                      18
```

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
cttggatcgc catacccctc                                              20

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
gggctccggg ttgtagattc                                              20

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
gaggaccaca ttgtgagggt                                              20

<210> SEQ ID NO 23
<211> LENGTH: 21
<212> TYPE: DNA
<213> ORGANISM: Artificial Sequence
<220> FEATURE:
<223> OTHER INFORMATION: synthetic

<400> SEQUENCE: 23
cgggtgatgt tgtaatccca g                                            21

<210> SEQ ID NO 24
<211> LENGTH: 19
<212> TYPE: DNA
<213> ORGANISM: Artificial Sequence
<220> FEATURE:
<223> OTHER INFORMATION: synthetic

<400> SEQUENCE: 24
cgacgagggg ttgtgtctg                                               19

<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
acatagctat tggggcagcg                                              20

<210> SEQ ID NO 26
<211> LENGTH: 18
<212> TYPE: DNA
<213> ORGANISM: Artificial Sequence
<220> FEATURE:

<223> OTHER INFORMATION: synthetic

<400> SEQUENCE: 26
tcatccaaga tggccgcc                                                                 18

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
gccagcactt ctgtttcagc                                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
gaaatcacgg aggagtggca                                                               20

<210> SEQ ID NO 29
<211> LENGTH: 21
<212> TYPE: DNA
<213> ORGANISM: Artificial Sequence
<220> FEATURE:
<223> OTHER INFORMATION: synthetic

<400> SEQUENCE: 29
aacagctgtg aaaccacctc a                                                             21

<210> SEQ ID NO 30
<211> LENGTH: 22
<212> TYPE: DNA
<213> ORGANISM: Artificial Sequence
<220> FEATURE:
<223> OTHER INFORMATION: synthetic

<400> SEQUENCE: 30
cagggaatca atcaggtgac ga                                                            22

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
atgggggtgg aattcatcgg                                                               20

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
cagtgaagtg ctcgtctggt                                                               20

```
<210> SEQ ID NO 33
<211> LENGTH: 21
<212> TYPE: DNA
<213> ORGANISM: Artificial Sequence
<220> FEATURE:
<223> OTHER INFORMATION: synthetic

<400> SEQUENCE: 33
cgactcaatc ccatacaccg t                                              21

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
aagccaagct tccgctatca                                                20

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
cgatgacagt caggtccgtg                                                20
```